United States Patent
Lim et al.

(10) Patent No.: US 10,617,662 B2
(45) Date of Patent: *Apr. 14, 2020

(54) AUTOPHAGY ACTIVATION-INDUCED COMPOUND FOR IMPROVING SKIN INFLAMMATION FOR AGING

(71) Applicant: INCOSPHARM CORPORATION, Daejeon (KR)

(72) Inventors: Chaejin Lim, Daejeon (KR); Heung Jae Kim, Daejeon (KR); Hwa-Jee Chung, Daejeon (KR); Juyeon Jung, Sejong (KR); Kayoung Shin, Daejeon (KR); Beom Cheol Kim, Daejeon (KR); Seok Jeong Yoon, Daejeon (KR); Myung Ho Kor, Daejeon (KR); Seon Deok Kwon, Daejeon (KR); Keedon Park, Daejeon (KR)

(73) Assignee: INCOSPHARM CORPORATION, Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/308,689

(22) PCT Filed: Jun. 23, 2017

(86) PCT No.: PCT/KR2017/006670
§ 371 (c)(1),
(2) Date: Dec. 10, 2018

(87) PCT Pub. No.: WO2017/222345
PCT Pub. Date: Dec. 28, 2017

(65) Prior Publication Data
US 2019/0160033 A1    May 30, 2019

(30) Foreign Application Priority Data

Jan. 4, 2017 (KR) .......................... 10-2017-0001515

(51) Int. Cl.
| | | |
|---|---|---|
| A61K 31/197 | (2006.01) |
| A23L 33/10 | (2016.01) |
| A61P 17/06 | (2006.01) |
| A61K 8/44 | (2006.01) |
| A61K 9/00 | (2006.01) |
| A61K 47/06 | (2006.01) |
| A61K 47/12 | (2006.01) |
| A61K 47/26 | (2006.01) |
| A61K 47/32 | (2006.01) |
| A61Q 19/00 | (2006.01) |
| A61Q 19/10 | (2006.01) |
| C07C 237/12 | (2006.01) |
| A61Q 1/00 | (2006.01) |

(52) U.S. Cl.
CPC ............ *A61K 31/197* (2013.01); *A23L 33/10* (2016.08); *A61K 8/44* (2013.01); *A61K 8/442* (2013.01); *A61K 9/0014* (2013.01); *A61K 47/06* (2013.01); *A61K 47/12* (2013.01); *A61K 47/26* (2013.01); *A61K 47/32* (2013.01); *A61P 17/06* (2018.01); *A61Q 1/00* (2013.01); *A61Q 19/00* (2013.01); *A61Q 19/10* (2013.01); *C07C 237/12* (2013.01); *A23V 2002/00* (2013.01); *A61K 2800/74* (2013.01)

(58) Field of Classification Search
None
See application file for complete search history.

(56) References Cited

FOREIGN PATENT DOCUMENTS

| KR | 10-2012-0130631 A | 12/2012 |
| KR | 10-2013-0110914 A | 10/2013 |
| KR | 10-2013-0117501 A | 10/2013 |
| KR | 10-2014-0103603 A | 8/2014 |

OTHER PUBLICATIONS

Maria Xilouri, et al., entitled, "Boosting chaperone-mediated autophagy in vivo mitigates α-synuclein-induced neurodegeneration", Brain A Journal of Neurology 2013; 136; pp. 2130-2146.

Lin Qi, et al., entitled, "The Role of Chaperone-Mediated Autophagy in Huntingtin Degradation", PLOS ONE, www.plosone.org, Oct. 2012, vol. 7, Issue 10, 16 pages.

*Primary Examiner* — Jeffrey S Lundgren
*Assistant Examiner* — Tori Strong
(74) *Attorney, Agent, or Firm* — Nixon Peabody LLP; Thomas P. Pavelko

(57) ABSTRACT

Provided are a novel autophagy activation-inducing compound or salt thereof, and a use thereof, and particularly, a medicinal composition for treatment and prevention of neurodegenerative diseases, type II diabetes, or atopy or psoriasis dermatitis, a cosmetic composition for alleviation of aging or atopy or psoriasis dermatitis, and a food composition, including the compound capable of inducing autophagy activation or a pharmaceutically acceptable salt thereof.

23 Claims, 10 Drawing Sheets

[FIG. 1]
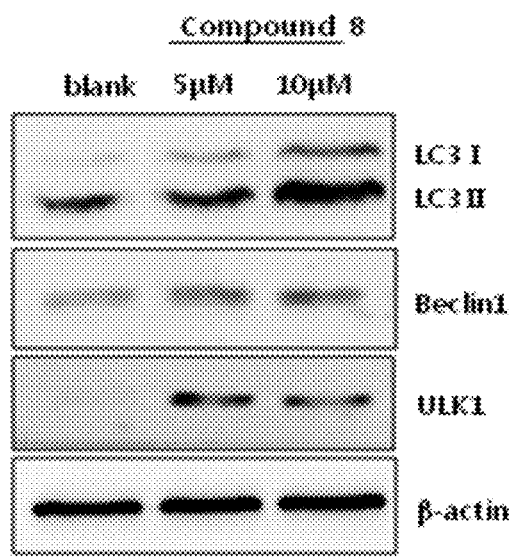
[FIG. 2]
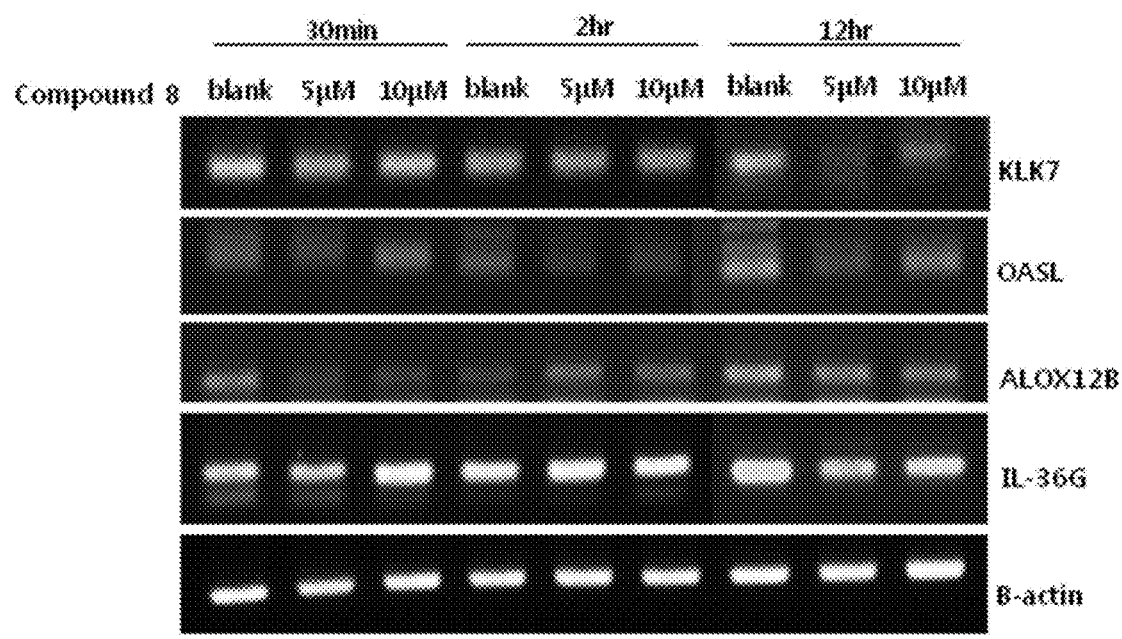

[FIG. 3]
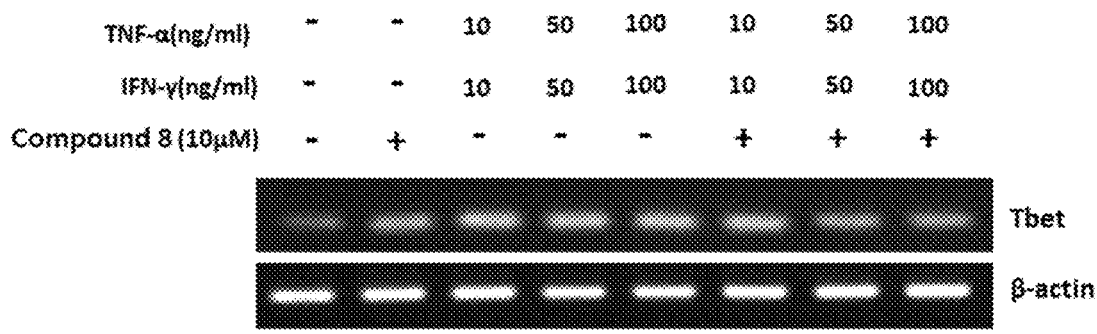
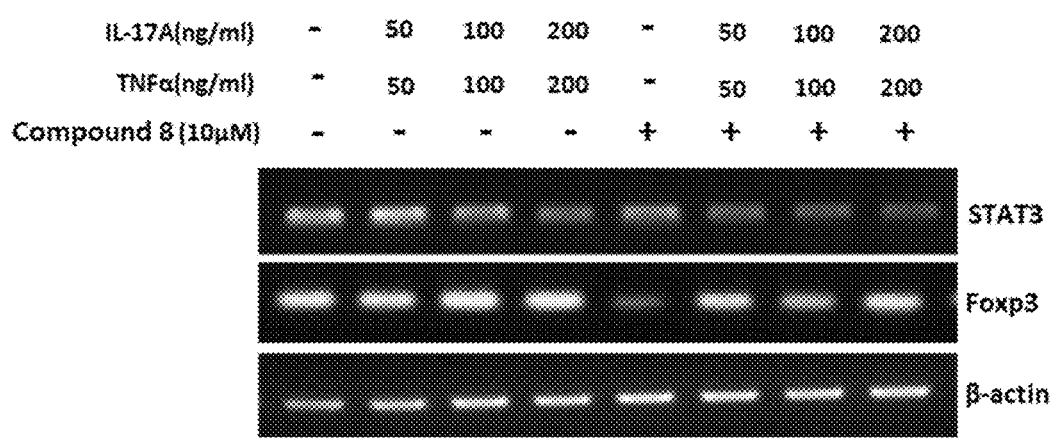
[FIG. 4]
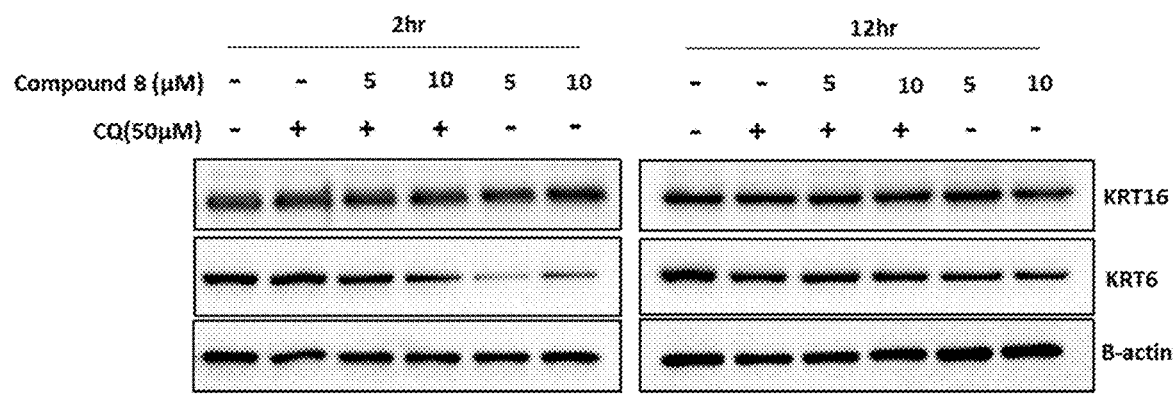

【FIG. 5】
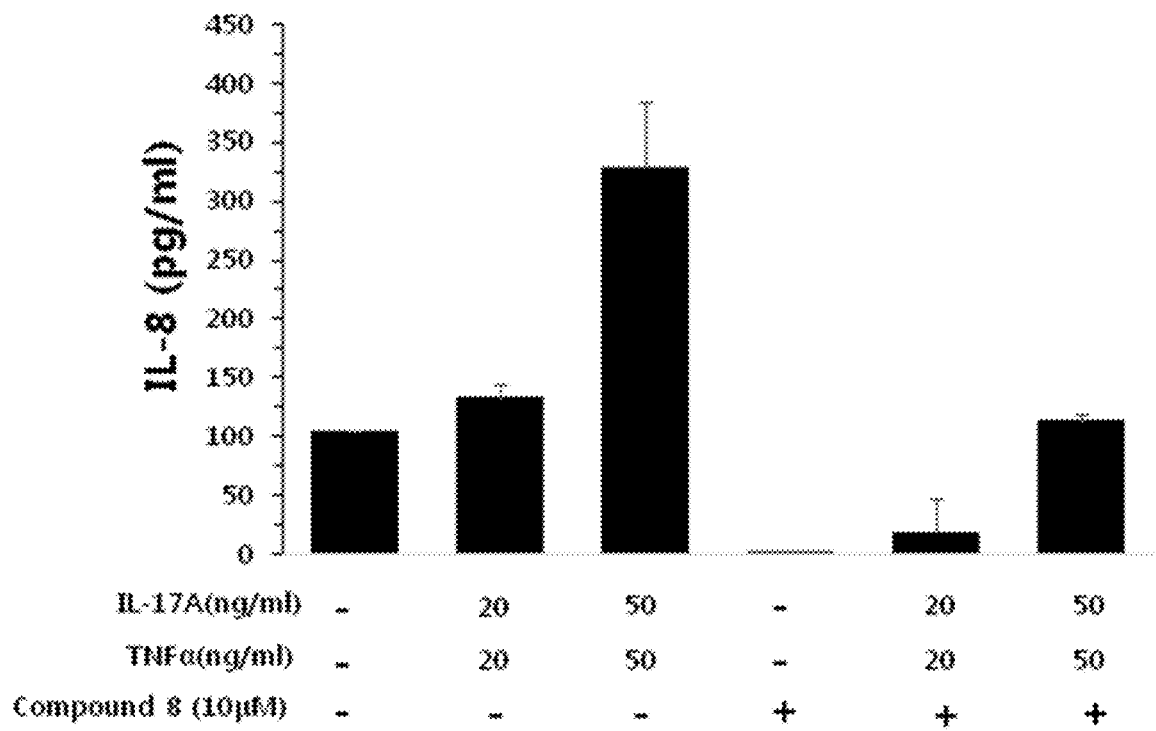
【FIG. 6】
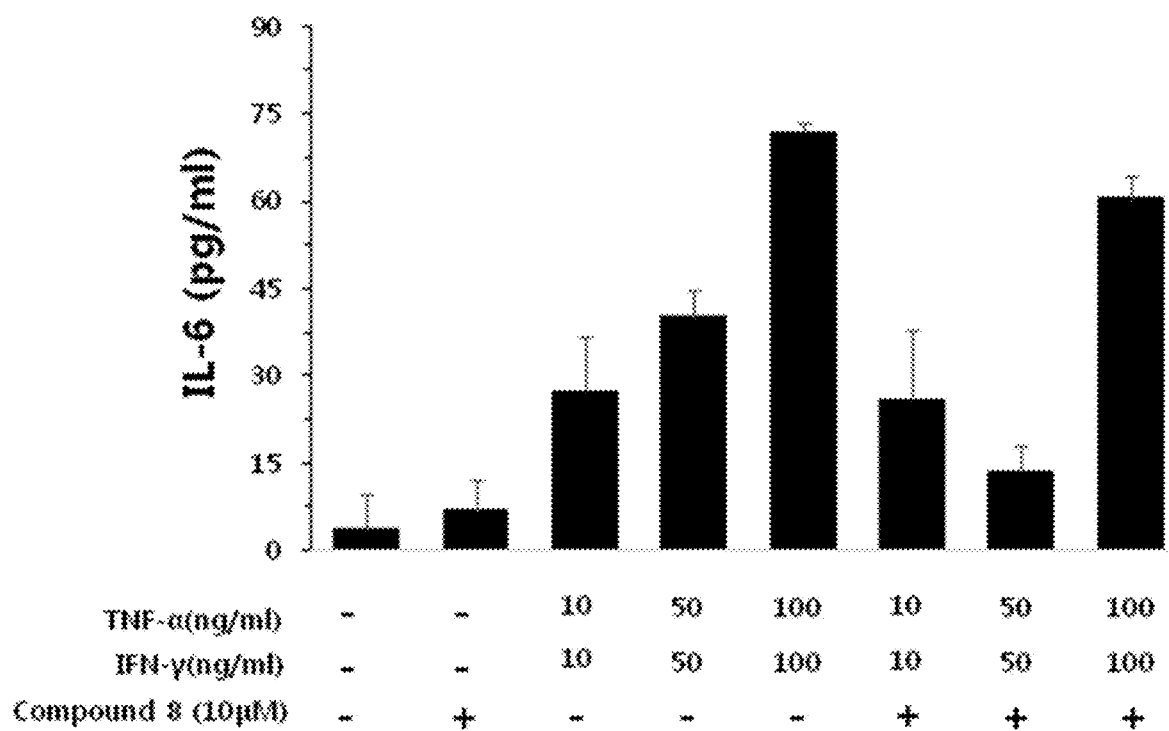

[FIG. 7]
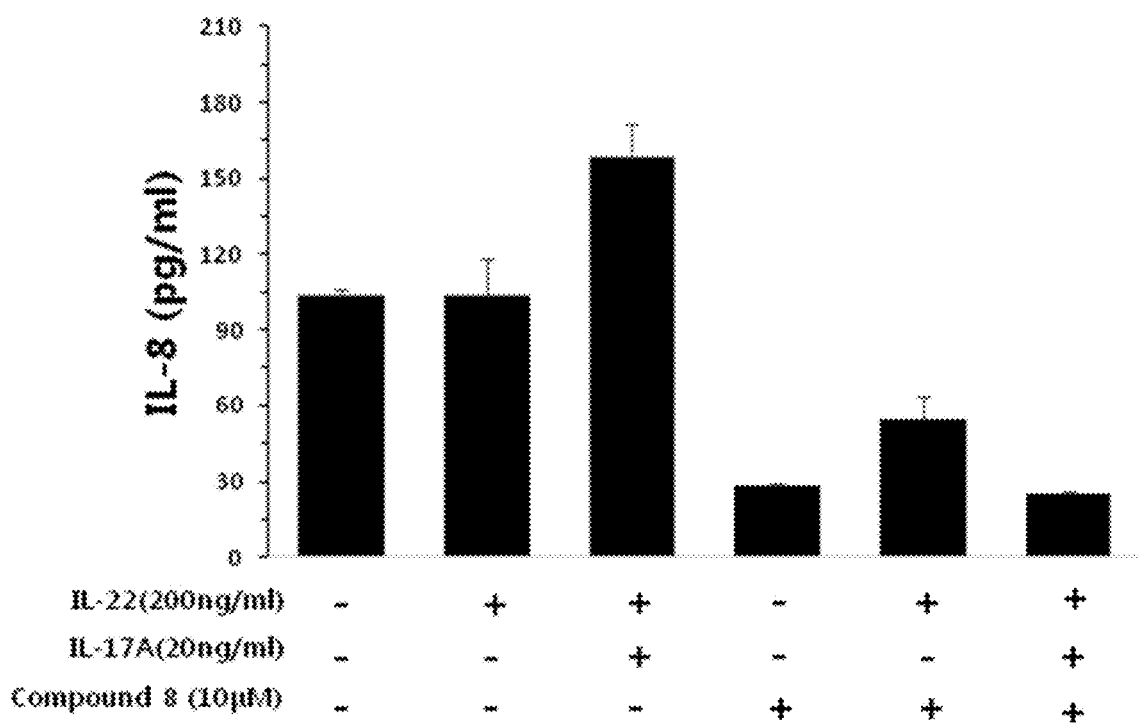
[FIG. 8]
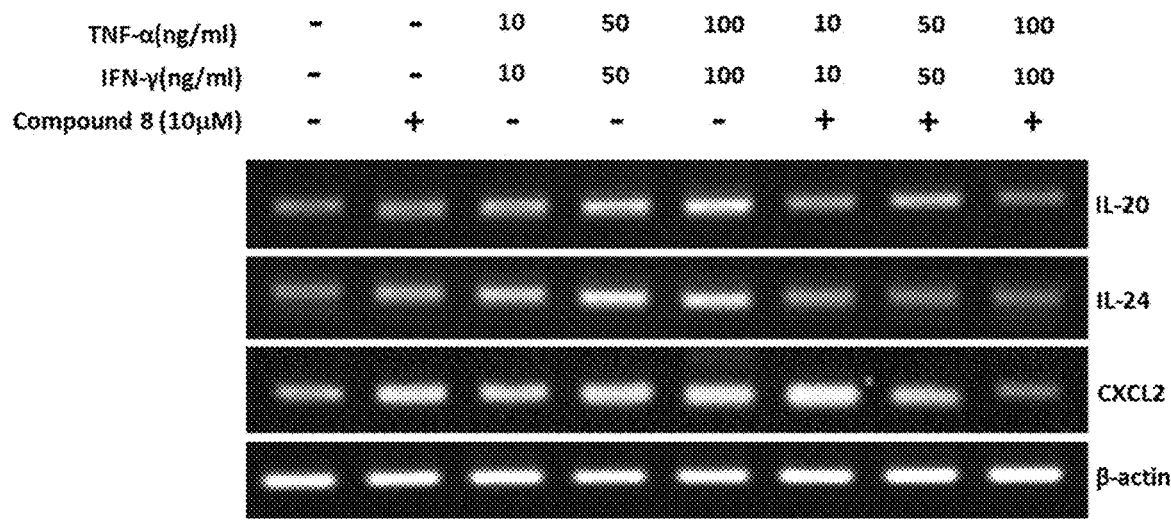

[FIG. 9]
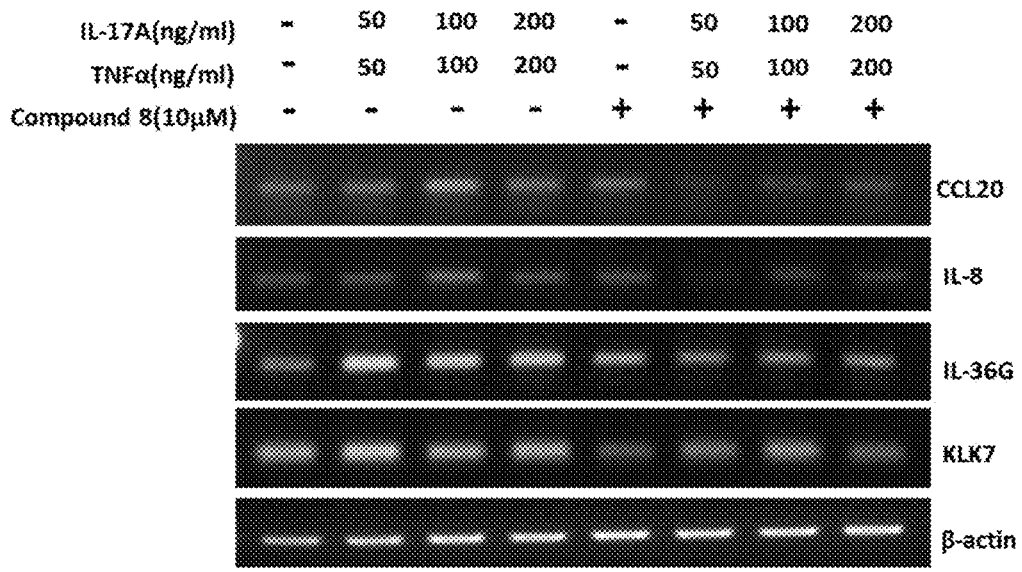
[FIG. 10]
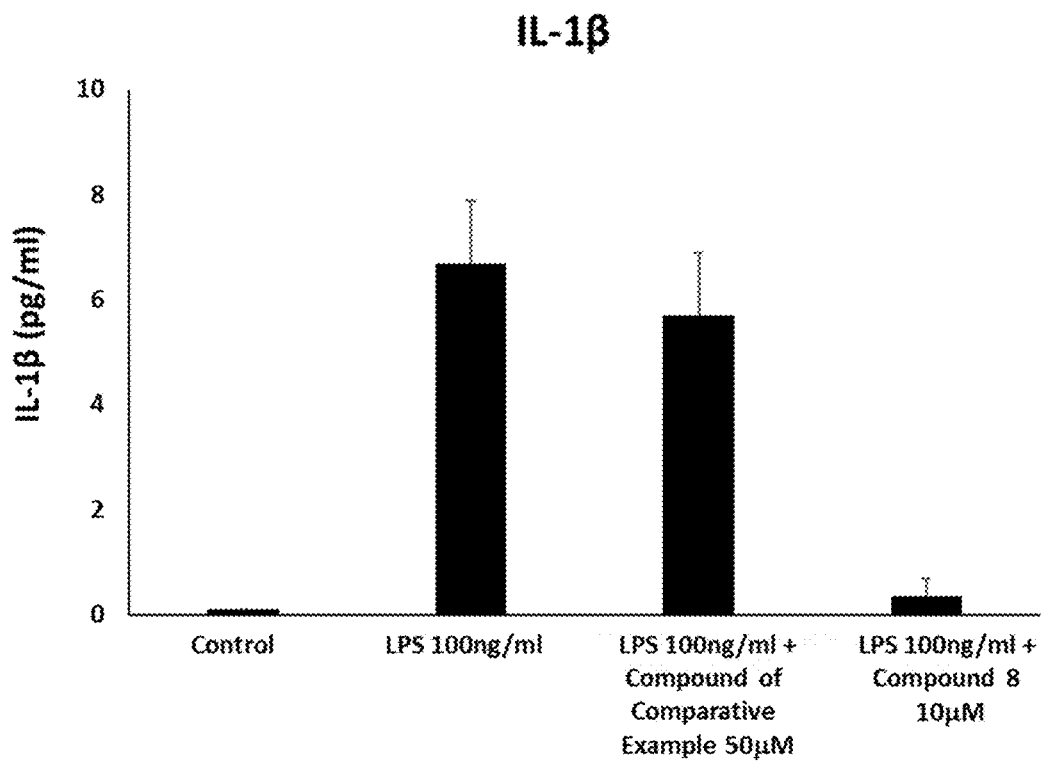

[FIG. 11]
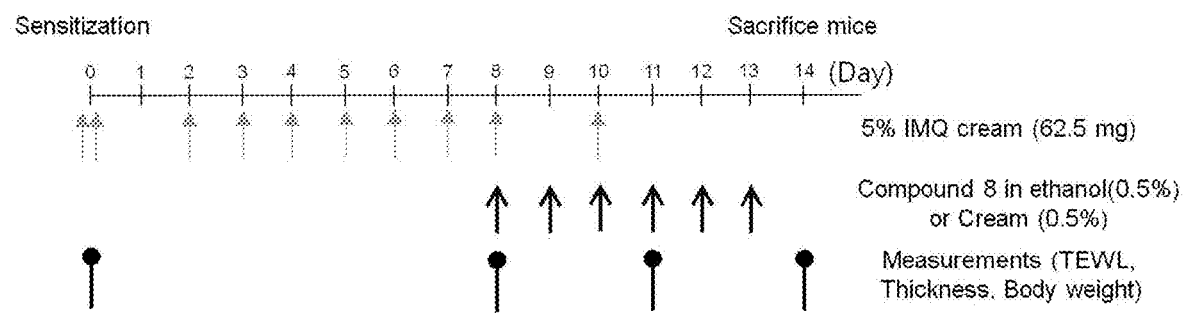
[FIG. 12]
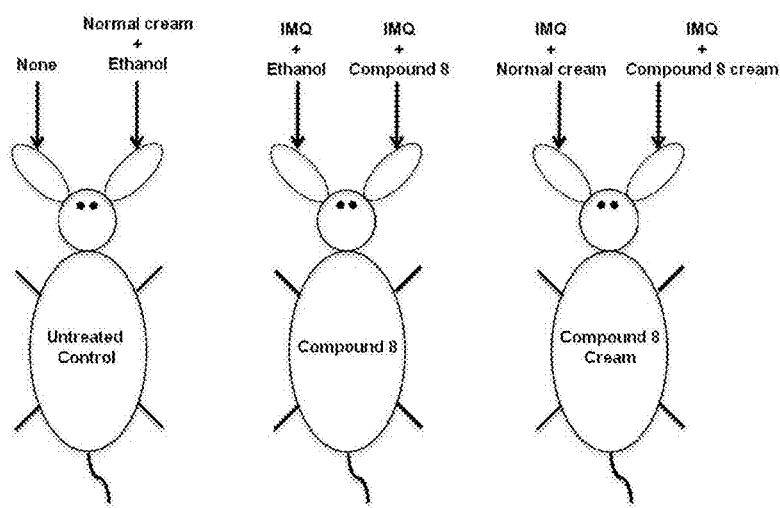

[FIG. 13]
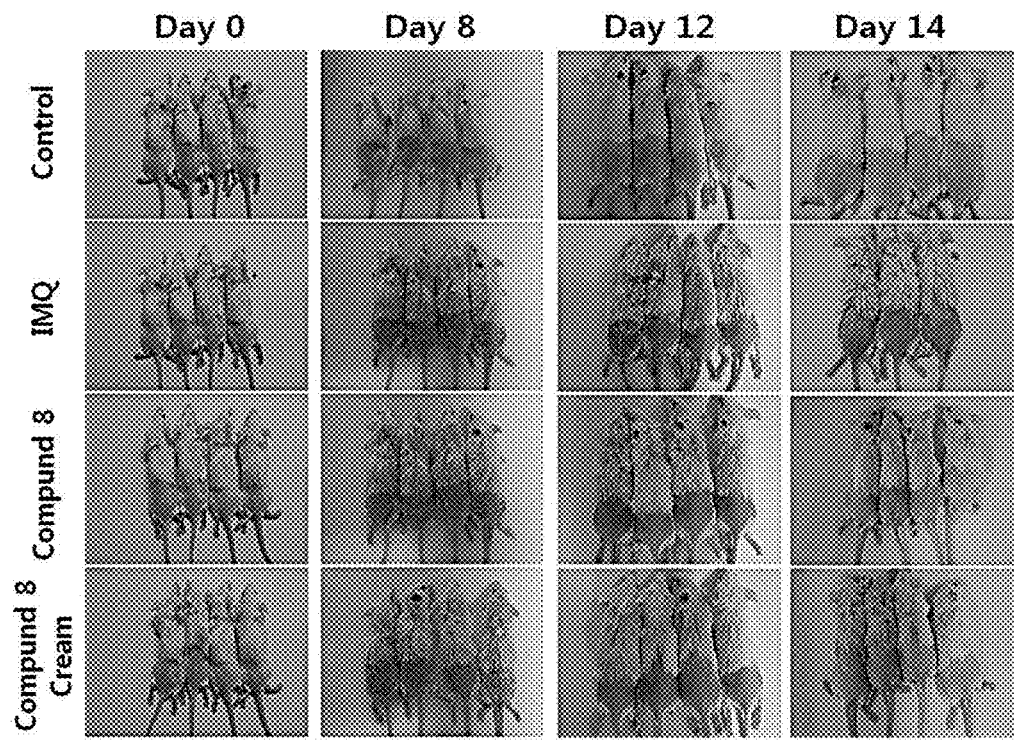
[FIG. 14]
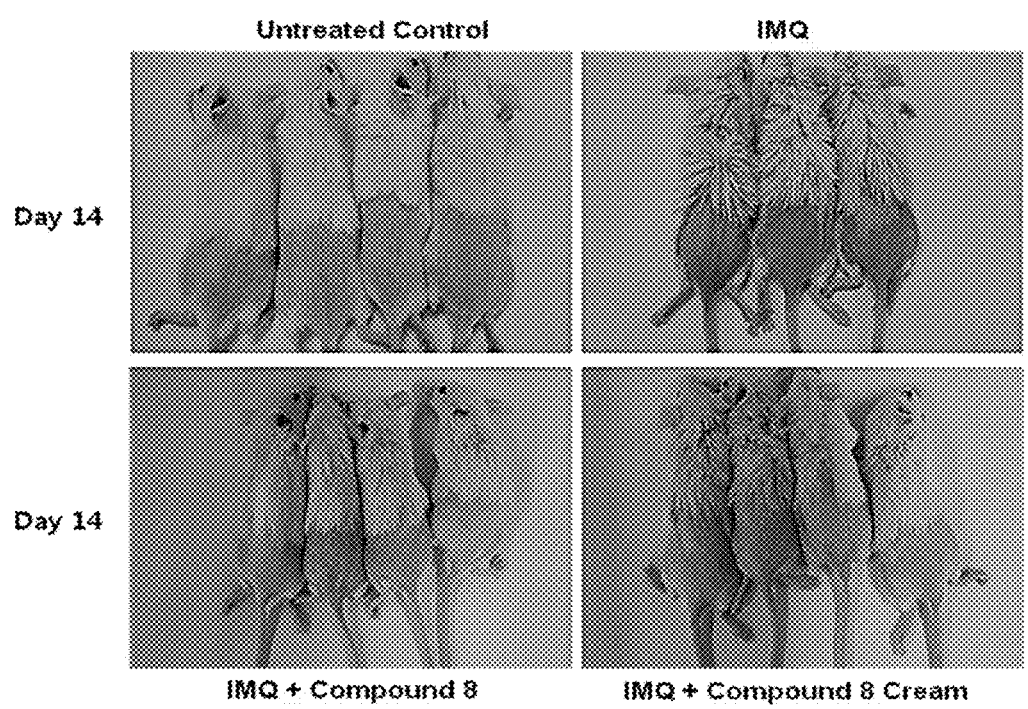

[FIG. 15]
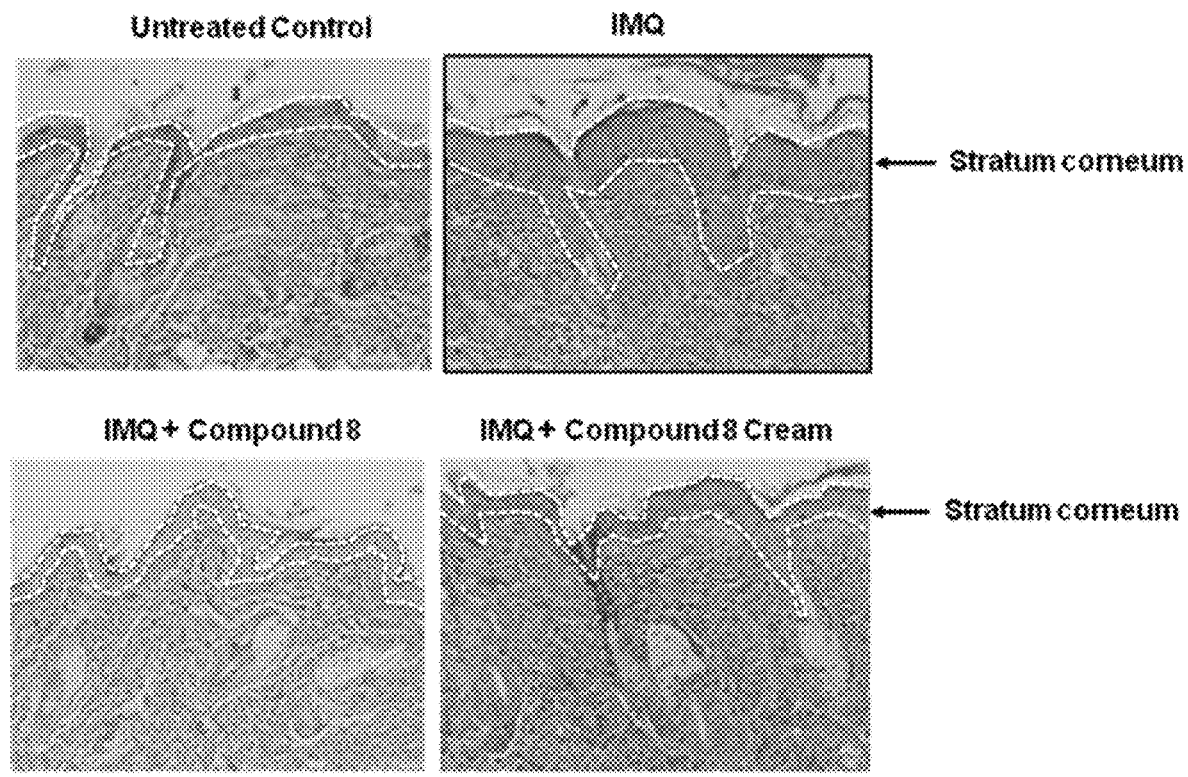

[FIG. 16]
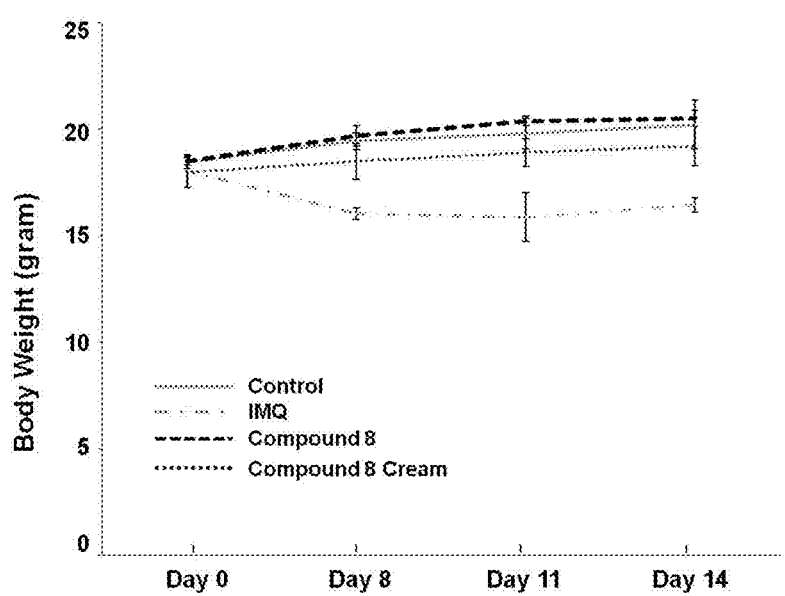

[FIG. 17]
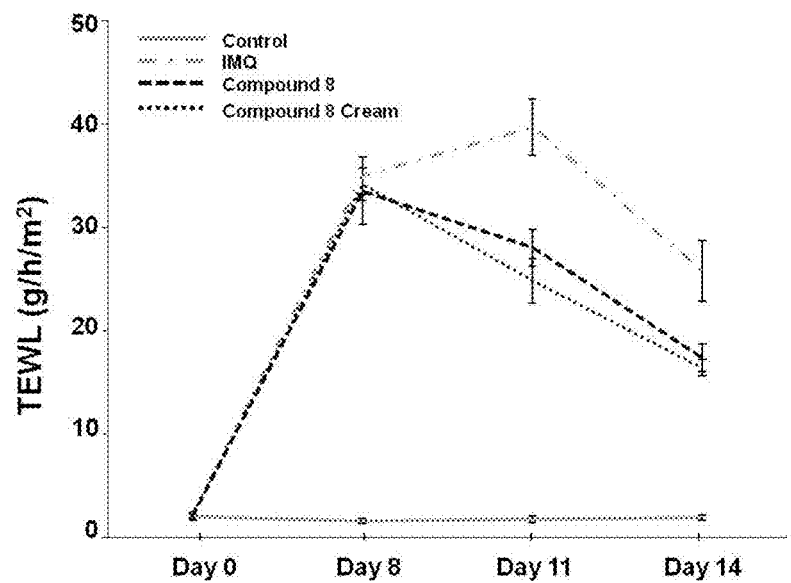
[FIG. 18]
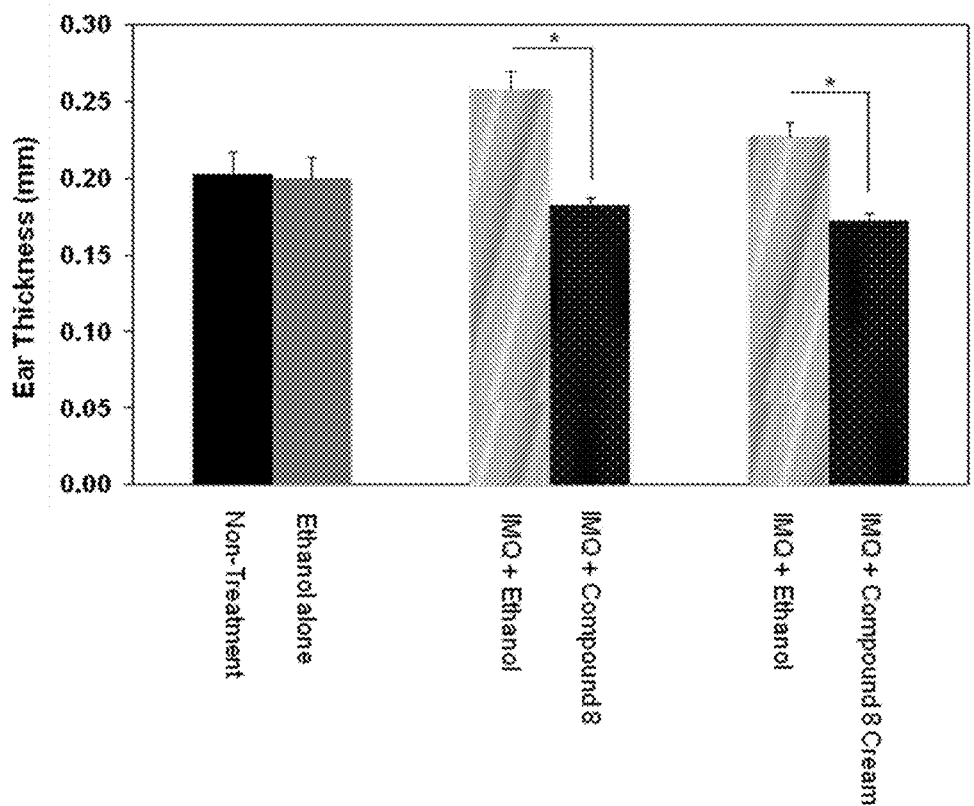

AUTOPHAGY ACTIVATION-INDUCED COMPOUND FOR IMPROVING SKIN INFLAMMATION FOR AGING

This application is the United States National Phase filed under 35 U. S. C. § 365 of International Application filed under the Patent Cooperation Treaty ("PCT") serial number PCT/KR2017/006670, filed on Jun. 23, 2017, which in turn claims priority from KR application serial number 10-2016-0079506, filed Jun. 24, 2016 and KR application serial number 10-2017-0001515 filed Jan. 4, 2017, the priorities of all of which are claimed under 35 U. S. C. § 119, and the contents of which are herein incorporated by reference.

TECHNICAL FIELD

The present invention relates to a novel compound and a use thereof, and more particularly, to a compound having an excellent autophagy activation ability, thereby being applied to prevention and treatment of various aging-related metabolic diseases, and inflammatory skin diseases such as atopy and psoriasis, or a pharmaceutically acceptable salt thereof, and a use thereof.

BACKGROUND ART

The cause of psoriasis and atopic skin diseases has not been revealed clearly; however, those diseases are evaluated as allergic skin diseases. Atopic dermatitis is regarded as being related to genetic factors and immune system deficiency. Other than that, it has been reported that dry skin, characteristics of easily feeling itchy as compared with normal people, or emotional and environmental factors occur in combination with one another.

Atopic dermatitis patient-related lesion is related to overproduction of IL-6, IL-8 and IL-10 by a Th2-cell mediated immune response, and increased concentration of serum immunoglobulin (IgE), and decreased production of interferon-gamma (IFN-γ). Psoriasis is an immune-mediated-autoimmune skin disease induced by chronic activation of inflammatory cell infiltration in skin and control disorder of epidermal keratinocytes. According to the existing reports, it has been reported to be related to a complex mechanism including interaction between inflammatory cytokine and immune cellular infiltration such as T cells, and recently, it has been reported that not only Th1 cells, but also Th17 cells and Th-17-mediated cytokines such as IL-17A and IL-22 induce psoriasis promotion.

Meanwhile, autophagy refers to a mechanism to degrade aged or damaged intracellular constituents and organelles when intracellular energy source is depleted or intracellular stress factors are excessively generated, thereby regenerating energy and removing damaged constituents, and allows maintenance of normal cells. Recently, it has been reported through various studies that as aging proceeds, or aging is accelerated, intracellular autophagy activation is rapidly reduced. In addition, when the autophagy inhibition is occurred, the aged mitochondria and misfolded protein or the like is excessively accumulated in cells that results in the increases of free radicals and oxidative stress in cells, eventually leading to apoptosis and aging promotion.

Therefore, unfolded or misfolded proteins, excessive lipid droplets, damaged mitochondrias and the like are rapidly removed by activation of an autophagic mechanism which degrades intracellular aged constituents and organelles and recycles the decomposed product therefrom, thereby providing the environment where cells may survive in a more healthy state.

It is known from preceding reports that the autophagy modulation can be applied for the treatment and prevention of type II diabetes, as well as neurodegenerative diseases such as Alzheimer's disease, Huntington's disease and Parkinson's disease.

In addition, the autophagy maintains intracellular homeostasis, and is also related to an immune cell response and an inflammatory pathway. A mechanism for removing intracellular microorganisms is provided by autophagic adapters. Thus, there is a need to develop an autophagy activation material to treat and prevent neurodegenerative diseases and type II diabetes, and alleviate skin inflammation, by promoting intracellular autophagy activation.

RELATED ART DOCUMENT

Non-patent Document

Hung et al. Autophagy, 2009, 5, 4, 502-510

Qi et al. PLOS one, 2012, 7, 10, e46834

Xilouri et al. Brain, 2013, 136, 2130-2146

Kim et al. The Journal of Clinical Investigation, 2014, 124, 8, 3311-3324

DISCLOSURE

Technical Problem

An object of the present invention is to provide a novel autophagy activation-inducing compound, and a pharmaceutically acceptable salt thereof.

In addition, another object of the present invention is to provide a medicinal composition for treatment and prevention of neurodegenerative diseases, type II diabetes, and inflammatory skin diseases such as atopy or psoriasis, including the autophagy activation-inducing compound of the present invention and the pharmaceutically acceptable salt thereof as an effective component.

In addition, another object of the present invention is to provide a cosmetic composition including the autophagy activation-inducing compound of the present invention and the pharmaceutically acceptable salt thereof.

In addition, still another object of the present invention is to provide a food composition including the autophagy activation-inducing compound of the present invention and the pharmaceutically acceptable salt thereof.

Technical Solution

In one general aspect, a compound inducing intracellular autophagy activation, or pharmaceutically acceptable salt thereof are provided, wherein the compound of the present invention is represented by the following Chemical Formula 1:

[Chemical Formula 1]

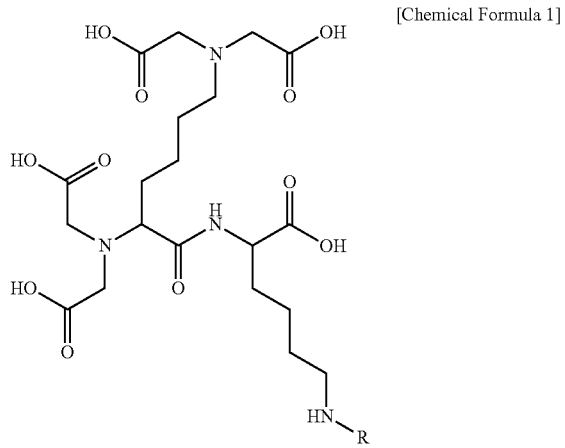

wherein

R is hydrogen or —X—$R^1$; X is a single bond or —CO—; and $R^1$ is (C1-C20) substituted or unsubstituted alkyl, e.g. C2-C18 substituted or unsubstituted alkyl, e.g., C3-C17 substituted or unsubstituted alkyl. In and exemplary embodiment, the $R^1$ is C13-C17 substituted or unsubstituted alkyl. In a further exemplary embodiment, $R^1$ is C15 substituted or unsubstituted alkyl. In various embodiments, $R^1$ is C15 unsubstituted alkyl.

Chemical Formula 1 according to an exemplary embodiment of the present invention may be represented by the following Chemical Formula 2:

[Chemical Formula 2]

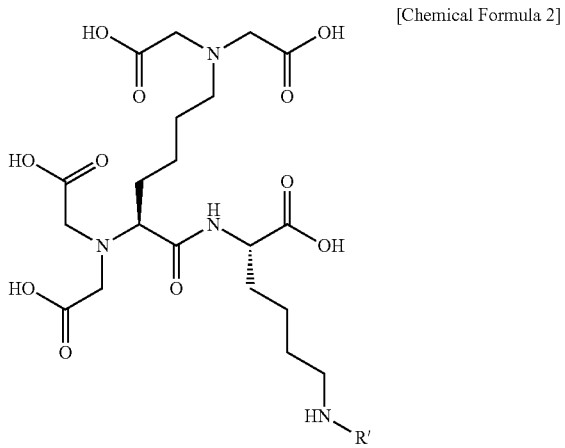

wherein

R' is hydrogen or —X—$R^2$; X is a single bond or —CO—; and $R^2$ is (C1-C20) alkyl. substituted or unsubstituted alkyl, e.g. C2-C18 substituted or unsubstituted alkyl, e.g., C3-C17 substituted or unsubstituted alkyl. In and exemplary embodiment, the $R^2$ is C13-C17 substituted or unsubstituted alkyl. In a further exemplary embodiment, $R^2$ is C15 substituted or unsubstituted alkyl. In various embodiments, $R^2$ is C15 unsubstituted alkyl.

Preferably, in Chemical Formula 2 according to an embodiment of the present invention, X may be —CO—, and $R^2$ may be (C1-C20) alkyl.

In addition, another object of the present invention is to provide a medicinal composition for treatment and prevention of neurodegenerative diseases, type II diabetes, or inflammatory skin diseases such as atopy and psoriasis, including the autophagy activation-inducing compound represented by Chemical Formula 1 or pharmaceutically acceptable salt thereof of the present invention as an effective component.

The neurodegenerative diseases according to an embodiment of the present invention may be Alzheimer's disease, Huntington's disease or Parkinson's disease.

Preferably, the medicinal composition according to an embodiment of the present invention may include the autophagy activation-inducing compound represented by Chemical Formula 1 or pharmaceutically acceptable salt thereof at 0.0001 to 10 wt %, and may be used in the form of tablets, pills, capsules, granules, pulverized forms, powders, liquid, patches or injections.

In addition, a cosmetic composition including the autophagy activation-inducing compound represented by Chemical Formula 1 or pharmaceutically acceptable salt thereof of the present invention is provided.

Preferably, the cosmetic composition according to an exemplary embodiment of the present invention may include 0.0001 to 1 wt % of the autophagy activation-inducing compound represented by Chemical Formula 1 or pharmaceutically acceptable salt thereof, and may be a formulation of suspension, emulsion, paste, gel, cream, lotion, powder, soap, surfactant-containing cleansing, oil, powder foundation, emulsion foundation, wax foundation or spray.

In addition, a food composition including the autophagy activation-inducing compound represented by Chemical Formula 1 or pharmaceutically acceptable salt thereof of the present invention is provided.

Advantageous Effects

The novel autophagy activation-inducing compound represented by Chemical Formula 1 or pharmaceutically acceptable salt thereof of the present invention may increase the expression of autophagy-related protein to activate autophagy, thereby protecting cells from oxidative stress, and remedying, preventing and treating various diseases and phenomena caused by oxidative stress.

The medicinal composition of the present invention includes the autophagy activation-inducing compound of the present invention which induces autophagy activation or the pharmaceutically acceptable salt thereof, thereby being very effective in treatment and prevention of autophagy-related diseases, in particular psoriasis, atopic dermatitis, neurodegenerative diseases or type II diabetes.

The cosmetic composition (in particular for alleviation and treatment of psoriasis and atopic dermatitis) and the food composition of the present invention may also include the autophagy activation-inducing compound of the present invention which increases the expression of autophagy-related proteins, or the pharmaceutically acceptable salt thereof, thereby protecting cells, tissues and organs from oxidative stress, and thus, are very effective in anti-inflammation.

DESCRIPTION OF DRAWINGS

The above and other objects, features and advantages of the present invention will become apparent from the following description of preferred embodiments given in conjunction with the accompanying drawings, in which:

FIG. 1 is a result of analyzing autophagy activation and protein expression related thereto by treatment of Compound 8 of the present invention.

FIGS. 2 to 4 are results of analyzing gene expression and protein expression of atopy- and psoriasis-related markers by Compound 8 of the present invention.

FIGS. 5 to 7 are results of an immunoassay of cytokine IL-6 (interleukin-6) and IL-8 (interleukin-8) appearing in atopy and psoriasis immune response by Compound 8 of the present invention.

FIGS. 8 and 9 are results of analyzing gene expression of cytokine appearing in atopy and psoriasis immune response.

FIG. 10 is a comparison result of the effect of Compound 8 of the present invention and the compound of the Comparative Example on cytokine IL-1. (Interleukin-1 beta) represented in atopy and psoriasis immune responses, using an immunoassay.

FIGS. 11 and 12 are schematic diagrams showing the entire process and the specific experimental method of a psoriasis animal model experiment.

FIGS. 13 to 15 are clinical and histological results in the psoriasis animal model by Compound 8 of the present invention.

FIG. 16 is a result of analysis of weight change after treating a psoriasis animal model with Compound 8 of the present invention.

FIG. 17 is a result of analysis of transepidermal water loss (TEWL) after treating a psoriasis animal model with Compound 8 of the present invention.

FIG. 18 is a result of analysis of thickness change of ear skin after treating the ears of a psoriasis animal model with Compound 8 of the present invention as in FIG. 12.

DEFINITIONS

The term "alkyl," by itself or as part of another substituent, means, unless otherwise stated, a straight or branched chain, or cyclic hydrocarbon radical, or combination thereof, which may be fully saturated, mono- or polyunsaturated and can include mono-, di- and multivalent radicals, having the number of carbon atoms designated (i.e., $C_1$-$C_{10}$ means one to ten carbons). Examples of saturated alkyl radicals include, but are not limited to, groups such as methyl, methylene, ethyl, ethylene, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, includes "alkylene" and, optionally, those derivatives of alkyl defined in more detail below, such as "heteroalkyl."

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, P and S, and wherein the nitrogen and sulfur atoms may optionally be oxidized and the nitrogen heteroatom may optionally be quaternized. The heteroatom(s) O, N, S, P and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R' represents both —C(O)$_2$R' and —R'C(O)$_2$.

The terms "cycloalkyl" and "heterocycloalkyl", by themselves or in combination with other terms, represent, unless otherwise stated, cyclic versions of "alkyl" and "heteroalkyl", respectively. Also included are di- and multivalent species such as "cycloalkylene." Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

Exemplary "Alkyl", "alkoxy" and other substituents containing an "alkyl" moiety described herein include both straight chain and branched chain forms, and have 1 to 20 carbon atoms, preferably 1 to 17, more preferably 1 to 15 carbon atoms.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, species such as trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Also included are di- and multi-valent linker species, such as "arylene." Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", OC(O)R', —C(O)R', —CO$_2$R', —CONR'R", —OC(O) NR'R", —NR"C(O)R', SO$_3$R', NR'C(O) NR"R'", —NR"C(O)$_2$R', —NR—C(NR'R"R'")=NR"", NRC(NR'R")=NR'", —S(O)R', —S(O)$_2$R', —S(O)$_2$NR'R", NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. Accordingly, from the above discussion of substituents, one of skill in the art will understand that the terms "substituted alkyl" and "heteroalkyl" are meant to include groups that have carbon atoms bound to groups other than hydrogen atoms, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

The substituents set forth in the paragraph above are referred to herein as "alkyl group substituents." Similar to the substituents described for the alkyl radical, substituents for the aryl and heteroaryl groups are varied and are selected from, for example: halogen, OR', =O, =NR', =N—OR', —NR'R", —SR', -halogen, —SiR'R"R'", OC(O)R', —C(O)R', CO$_2$R', —CONR'R", —OC(O)NR'R", —NR"C(O)R', NR'C(O) NR"R'", —NR"C(O)$_2$R', NRC(NR'R")=NR'", —S(O)R', —S(O)$_2$R', SO$_3$R', —S(O)$_2$NR'R", NRSO$_2$R', —CN and —NO$_2$, —R', —N$_3$, —CH(Ph)$_2$, fluoro (C$_1$-C$_4$) alkoxy, and fluoro (C$_1$-C$_4$) alkyl, in a number ranging from zero to the total number of open valences on the aromatic ring system; and where R', R", R'" and R"" are preferably independently selected from hydrogen, (C$_1$C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A(CH$_2$)$_r$B—, wherein A and B are independently —CRR'—, —O—, —NR—, —S—, —S(O)—, S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl. The substituents set forth in the two paragraphs above are referred to herein as "aryl group substituents."

[Best Mode]

Hereinafter, the embodiments of the present invention will be described in detail with reference to accompanying drawings.

The present invention provides an autophagy activation-inducing compound represented by the following Chemical Formula 1 or pharmaceutically acceptable salt thereof which may induce autophagy activation to be effectively used in various uses:

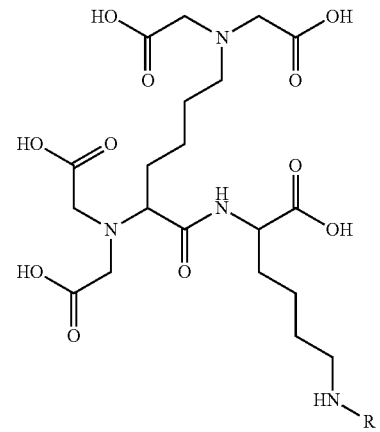

[Chemical Formula 1]

wherein

R is hydrogen or —X—R$^1$; X is a single bond or —CO—; and R$^1$ is (C1-C20) substituted or unsubstituted alkyl, e.g. C2-C18 substituted or unsubstituted alkyl, e.g., C3-C17 substituted or unsubstituted alkyl. In an exemplary embodiment, R$^1$ is C13-C17 substituted or unsubstituted alkyl. In a further exemplary embodiment, R$^1$ is C15 substituted or unsubstituted alkyl. In various embodiments, R$^1$ is C15 unsubstituted alkyl.

Intracellular autophagy activation actively occurs in tissues and cells of young people, but as the aging proceeds, the expression of intracellular autophagy-related proteins is rapidly decreased. Thereby the autophagy activity is rapidly decreased, and thus, intracellular aged protein, lipid and mitochondria are not removed timely, so that a cellular aging rapidly occurs.

Therefore, autophagy is activated, thereby inhibiting aging of each cell, tissue and organ, and allowing treatment of various diseases caused by aging.

In addition, the activation of autophagy improves aged cell viability through removal of intracellular harmful protein and organelles, and moreover, is closely associated with increased lifetime of each individual.

According to the reports of the prior art, the activation of autophagy reduces beta-amyloid accumulation, a main cause of Alzheimer's disease, and thus provides an effect of protecting cells from cytotoxicity therefrom, thereby minimizing damage of nerve cells (Hung et al. Autophagy, 2009, 5, 4, 502-510). And the activation of autophagy degrades and removes mutant huntingtin (htt) protein, a main cause of Huntington's disease, thereby alleviating symptom and treating Huntington's disease (Qi et al. PLOS one, 2012, 7, 10, e46834)., And the activation of autophagy provides an effect of inhibiting accumulation of alpha-synuclein, a main cause of Parkinson's disease, thereby alleviating neurodegeneration (Xilouri et al. Brain, 2013, 136, 2130-2146). Moreover, the activation of autophagy removes a toxic oligomer of human pancreatic amyloid polypeptide that causes type II diabetes by destroying pancreatic beta cells, thereby alleviating symptom and treating type II diabetes (Kim et al. The Journal of Clinical Investigation, 2014, 124, 8, 3311-3324).

In addition, it has been recently reported that an incidence of dermatitis such as atopic dermatitis, psoriasis and acne, or dermatopathy due to environmental contamination are increasing. Though a precise mechanism of the onset of these diseases has not been elucidated yet, it is widely accepted that cytokines regulate immunity and skin inflammation by sending downstream signals to various cells through a number of signal transduction pathways and by binding to cytokine receptors on the surface of cells, and thereby resulting in the hyperplasia of keratinocyte and the inhibition of keratinocyte differentiation (Arijit Coondoo, Indian J Dermatol, 57, 90-96, 2012).

Thus, the present inventors made an effort in order to develop a material of promoting autophagy activation, and as a result, found that the compound represented by Chemical Formula 1 has an effect of autophagy activation by increasing autophagy-related gene transcription and protein expression in cells, and has an important role in suppressing secretion of inflammatory cytokines, thereby completing the present invention.

Consequently, the autophagy activation-inducing compound represented by the following Chemical Formula 1 or pharmaceutically acceptable salt thereof of the present invention has an effect of increasing expression of autophagy activation-related protein, and activating autophagy, and thus, a composition including them may be very useful for anti-aging, or prevention, remedy or treatment of neurodegenerative diseases (Alzheimer's disease, Huntington's disease, Parkinson's disease, etc.), type II diabetes, or dermatitis such as psoriasis and atopic dermatitis.

Preferably, the autophagy activation-inducing compound represented by Chemical Formula 1 according to an exemplary embodiment of the present invention may be represented by the following Chemical Formula 2:

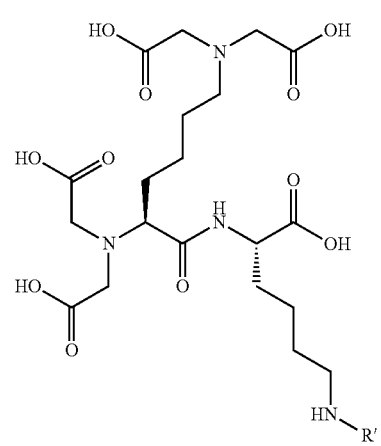

[Chemical Formula 2]

wherein

R' is hydrogen or —X—$R^2$; X is a single bond or —CO—; and $R^2$ is (C1-C20) substituted or unsubstituted alkyl, e.g. C2-C18 substituted or unsubstituted alkyl, e.g., C3-C17 substituted or unsubstituted alkyl. In an exemplary embodiment, $R^2$ is C13-C17 substituted or unsubstituted alkyl. In a further exemplary embodiment, $R^2$ is C15 substituted or unsubstituted alkyl. In various embodiments, $R^2$ is C15 unsubstituted alkyl.

More preferably, in Chemical Formula 2 according to an exemplary embodiment of the present invention, X may be —CO—, and $R^2$ may be (C1-C20) substituted or unsubstituted alkyl, e.g. C2-C18 substituted or unsubstituted alkyl, e.g., C3-C17 substituted or unsubstituted alkyl. In an exemplary embodiment, $R^2$ is C3-C17 substituted or unsubstituted alkyl. In a further exemplary embodiment, $R^2$ is C15 substituted or unsubstituted alkyl. In various embodiments, $R^2$ is C15 unsubstituted alkyl.

Specifically, the autophagy activation-inducing compound represented by Chemical Formula 1 of the present invention may be represented by the following Chemical Formula 3:

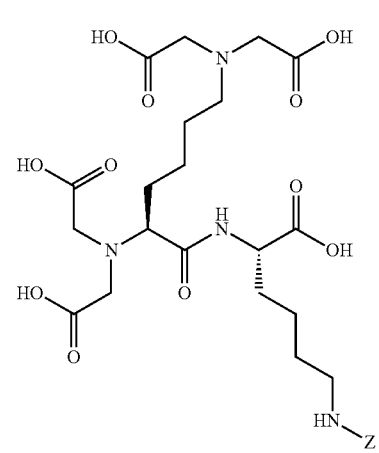

[Chemical Formula 3]

wherein
Z is hydrogen or

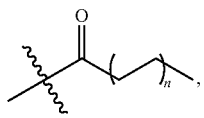

and n is an integer selected from 0, 1, 2, 3, 4, 5, 6 and 7.

Further, the present invention provides a medicinal composition for prevention or treatment of neurodegenerative diseases, type II diabetes, or psoriasis and atopic dermatitis, including the autophagy activation-inducing compound represented by Chemical Formula 1 or pharmaceutically acceptable salt thereof of the present invention.

Specifically, the medicinal composition of the present invention is very effective in prevention or treatment of Alzheimer's disease, Huntington's disease, Parkinson's disease, type II diabetes, psoriasis or atopic dermatitis caused by a toxic oligomer former of mutant alpha-amyloid, huntingtin, alpha-synuclein and human pancreatic amyloid polypeptide, by its autophagy activation function.

The neurodegenerative diseases according to an exemplary embodiment of the present invention may be Alzheimer's disease, Huntington's disease or Parkinson's disease.

The content of the autophagy activation-inducing compound or pharmaceutically acceptable salt thereof contained in the medicinal composition according to an exemplary embodiment of the present invention may be properly adjusted depending on a use, an application form, a use purpose and a desired effect of the composition, and considering the effect relative to the content, for example, it may be 0.0001 to 10 wt %, preferably 0.001 to 5 wt %, and most preferably 0.03 to 1 wt % based on the total weight of composition. When the content is lower than the above range, a substantial autophagy activation effect may not be obtained, and when the content is higher than the above range, the stability of a formulation may be deteriorated due to a high hygroscopic property of the present material, and thus, the above range is preferred.

The pharmaceutically acceptable salt of the compound of the present invention may be prepared using a common technique known in the art, and the term 'pharmaceutically acceptable salt' includes salts derived from pharmaceutically acceptable inorganic acids, organic acids or bases. Examples of the suitable acid may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, trifluoroacetic acid, citric acid, methanesulfonic acid, formic acid, benzoic acid, malonic acid, naphthalene-2-sulfonic acid, benzenesulfonic acid and the like. The salt derived from a suitable base may contain alkali metals such as sodium, alkali earth metals such as magnesium, ammonium and the like.

The medicinal composition of the present invention may be used mainly via oral, intravenous, intraperitoneal, intramuscular and subcutaneous administration methods. Further, it may be formulated into an oral formulation such as powders, granules, tablets, capsules, suspensions, emulsions, syrups and aerosols, external preparations, suppositories, sterile injection solutions, and the like by a common method, however, there is no particular limitation on the forms.

The medicinal composition of the present invention may further include a pharmaceutically acceptable additive commonly used in the preparation of a medicinal composition. The pharmaceutically acceptable additive refers to a carrier or diluent which neither significantly stimulates organisms nor inhibits the biological activity and properties and of an administered compound. In addition, the additive may improve the preparation, compression, appearance and taste of a preparation, and for example, a stabilizer, a surfactant, a lubricant, a solubilizer, a buffer, a sweetener, a base, an adsorbent, a flavor enhancer, a binder, a suspending agent, a hardener, an antioxidant, a brightener, a fragrance ingredient, a flavoring agent, a pigment, a coating agent, a wetting agent, a wetting adjusting agent, a filler, a defoamer, a refresher, a chewing agent, an antistatic agent, a coloring agent, a sugar coating agent, an isotonic agent, a softener, an emulsifier, a sticking agent, a thickener, a blowing agent, a pH regulator, an excipient, a dispersant, a disintegrant, a waterproofing agent, an antiseptic agent, a preservative, a dissolution aid, a solvent, a fluidizing agent and the like may be added as required.

As an example, a preparation for oral administration includes tablets, pills, powders, granules, capsules and the like, and this preparation may include at least one excipient and/or lubricant and the like. A liquid preparation for oral administration may be suspensions, oral liquids, emulsions, syrups, and the like, and include various excipients, for example, a wetting agent, a sweetener, an aromatic, a preservative, and the like, in addition to water and liquid paraffin which are a simple diluent to be commonly used. Further, a preparation for parenteral administration may include a sterile aqueous solution, a non-aqueous solvent, a suspension solvent, emulsion, a freeze-dried preparation, a suppository and the like.

A preferred dosage of the medicinal composition is varied with state and weight of a patient, severity of diseases, drug forms, an administration route and a duration, but may be properly selected by a person skilled in the art. For more preferred effect, it is preferred that the dosage of the composition of the present invention is 0.1 mg/kg to 100 mg/kg per day, based on an effective component, but not limited thereto. The administration may be once a day, or divided into several times a day. A pharmaceutically administered form of the medicinal composition of the present invention may be a form of a pharmaceutically acceptable salt of an effective component, and also, may be used alone, in combination with other pharmaceutically active compound, or as a proper aggregate.

The medicinal composition of the present invention may be administered orally or parenterally, and in the case of parenteral administration, intravenous injection, subcutaneous injection, intramuscular injection, intraperitoneal injection, transdermal administration and the like may be used.

The medicinal composition of the present invention may include a pharmaceutically acceptable carrier. The pharmaceutically acceptable carrier included in the medicinal composition of the present invention may be commonly used in preparation, and includes lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil and the like, but not limited thereto. The medicinal composition of the present invention may further include a lubricant, a wetting agent, a sweetener, a flavoring agent, an emulsifier, a suspending agent, a preservative and the like in addition to the above components.

The medicinal composition of the present invention may be formulated into a usual preparation using a pharmaceutically acceptable carrier and/or excipient, by a method which may be easily carried out by a person skilled in the art to which the invention pertains, thereby being prepared into a unit dosage form or prepared by being injected into a multi-volume vessel. The usual formulation refers to, for example, oral (tablets, capsules, powders), intrabuccal, sublingual, intrarectal, intravaginal, intranasal, topical or parenteral (including intravenous, intracavernosal, intramuscular, subcutaneous and intravenous) administration formulation. For example, the autophagy activation-inducing compound according to the present invention may be orally, intrabuccally or sublingually administered in the form of tablets containing starch or lactose, or capsules formed solely or containing an excipient, or elixirs or suspensions containing favoring or coloring chemicals. The liquid preparation may be prepared together with a pharmaceutically acceptable additive such as a suspension (e.g., methyl cellulose, semisynthetic glyceride such as witepsol, or a glyceride mixture such as a mixture of apricot kernel oil and PEG-6 ester or a mixture of PEG-8 and caprylic/capric glyceride). In addition, when it is parenterally, for example, intravenously, intracavernosally, intramuscularly, subcutaneously and intraluminally injected, it is most preferred to be used in the form of a sterile aqueous solution, wherein the solution may contain other materials (e.g., salts or monosaccharides such as mannitol or glucose) in order to have isotonicity with blood.

Preferably, the medicinal composition according to an exemplary embodiment of the present invention may be used in the form of tablets, pills, capsules, granules, pulverized forms, powders, liquids, patches or injection solutions.

In addition, the present invention provides a cosmetic composition including the autophagy activation-inducing compound represented by Chemical Formula 1 or pharmaceutically acceptable salt thereof of the present invention.

The cosmetic composition of the present invention is a functional cosmetic composition for alleviation and treatment of atopic dermatitis, or antiaging, and depending on the administration route, it may be a composition capable of being skin-externally, transdermally or subcutaneously administered, preferably, skin-externally or transdermally, more preferably skin-externally administered.

The cosmetic composition of the present invention refers to a composition which may be transdermally applied to skin, scalp, or hair, and may be used in preparation of all cosmetic products such as fundamental cosmetics, makeup cosmetics, body products, shaving products and hair products, and may be formulated into a suspension, an emulsion, paste, gel, cream, lotion, powder, soap, surfactant-containing cleansing, oil, powder foundation, emulsion foundation, wax foundation or spray, but the form is not particularly limited.

The content of the autophagy activation-inducing compound represented by Chemical Formula 1 contained in the cosmetic composition of the present invention may be properly adjusted depending on a use, an application form, a use purpose and a desired effect of the composition, and considering the effect relative to the content, for example, it may be 0.0001 to 1 wt %, preferably 0.001 to 0.5 wt %, and most preferably 0.03 to 0.1 wt %, based on the total weight of the composition. When the content is lower than the above range, a substantial autophagy activation effect may not be obtained, and when the content is higher than the above range, the stability of a formulation may be deteriorated due to a high hygroscopic property of the present material, and thus, the above range is preferred.

The cosmetic composition according to an exemplary embodiment of the present invention may further include all kinds of components usable in common productization or preparation, for example, flavorings, colorant, disinfectants, antioxidants, antiseptic agents, moisturizers, stabilizers, emulsifiers, thickeners, liquid crystal film reinforcing agents, pigments, excipients, diluents, inorganic salts and synthetic polymers and the like, in addition to the autophagy activation-inducing compound represented by Chemical Formula 1 or pharmaceutically acceptable salt thereof of the present invention, and the kind and content thereof may be properly adjusted depending on the use and use purpose of the final product.

The additive which may be further contained is not limited as long as it is a material commonly used in the art, and as a specific example thereof, antiseptic agents such as propanediol, 1,2-hexanediol, ethylhexyl glycerin, phenoxyethanol, caprylhydroxamic acid and glyceryl caprylate; UV absorbers such as methoxycinnamic acid derivative, diphenylacrylic acid derivative, salicylic acid derivative, paraaminobenzoic acid derivative, triazine derivative, benzophenone derivative, benzalmalonate derivative, anthranil derivative, imidazoline derivative, 4,4-diarylbutadiene derivative, and phenylbenzimidazole derivative systems; fatty alcohols such as cetearyl alcohol, cetyl alcohol and behenyl alcohol; and stabilizers selected from silicone polymers such as bis PEG-15/methylethyldimethyl silane, dimethicone/dimethicone PEGT-10/15, dimethicone/polyglycerin-3, dimethicone/dimethiconol, dimethicone/dimethicone vinyldimethicone, cyclomethicone/dimethiconol, cyclomethicone/dimethicone, cyclomethicone/trimethylsiloxysilicate, cyclopentasiloxane/dimethicone, cyclopentasiloxane/PEG-12 dimethicone, cyclopentasiloxane/cetearyl dimethicone/vinyl dimethicone, cyclopentasiloxane/dimethicone/vinyl dimethicone, and dimethicone/vinyl dimethicone crosspolymer; and emulsifiers selected from cationic surfactants, anionic surfactants, amphoteric surfactants, nonionic surfactants and the like may be mixed, and preferably, of course, it is also possible to directly prepare it by reacting polyglyceryl and fatty acid with a polyglyceryl fatty acid ester-based surfactant such as caprylate/caprate, polyglyceryl-6 caprylate/caprate, polyglyceryl-7 caprylate/caprate, polyglyceryl-8 caprylate/caprate, polyglyceryl-9 caprylate/caprate, polyglyceryl-10 caprylate/caprate, polyglyceryl-4 caprate, polyglyceryl-5 caprate, polyglyceryl-6 caprate, polyglyceryl-7 caprate, polyglyceryl-8 caprate, polyglyceryl-9 caprate, polyglyceryl-10 caprate, polyglyceryl-4 laurate, polyglyceryl-5 laurate, polyglyceryl-6 laurate, polyglyceryl-7 laurate, polyglyceryl-8 laurate, polyglyceryl-9 laurate, polyglyceryl-10 laurate, polyglyceryl-6 cocoate, polyglyceryl-7 cocoate, polyglyceryl-8 cocoate, polyglyceryl-9 cocoate, polyglyceryl-10 cocoate, polyglyceryl-11 cocoate, polyglyceryl-12 cocoate, polyglyceryl-6 myristate, polyglyceryl-7 myristate, polyglyceryl-8 myristate, polyglyceryl-9 myristate, polyglyceryl-10 myristate, polyglyceryl-11 myristate, polyglyceryl-12 myristate, polyglyceryl-10 oleate, polyglyceryl-11 oleate, polyglyceryl-12 oleate, polyglyceryl-10 stearate, polyglyceryl-11 stearate, polyglyceryl-12 stearate and polyglyceryl-6 behenate, or to purchase a commercially available product and use it. The thickener is for imparting suitable viscosity of a cosmetic composition to improve use feeling and stability of a formulation, and may be selected from carbomer, carbopol, gelatin, xanthan gum, natural cellulose, Hycel, methyl cellulose and the like, but not limited thereto. The liquid crystal film reinforcing agent serves to increase strength of liquid crystal, and tightly connect fences to maintain long-term stability of a liquid crystal, and may be phytosphingosine, bishydroxyethyl bis-cetyl maloamide, cholesterol isostearate, cholesterol oleate, cholesterol stearate, lecithin, ceramides (e.g., ceramide 3, ceramide 6) and the like, but not limited thereto.

In addition, the pigment includes an extender pigment, a white pigment, a coloring pigment, a pearlescent pigment, metal powder, organic powder and the like, the extender pigment may be talc, mica, kaolin, calcium carbonate, alumina, barium silicate, zeolite, muscovite, magnesium carbonate, barium sulfate and the like, the white pigment may be titanium oxide, zinc oxide and the like, the coloring pigment may be red oxide, iron sulfate, iron oxide black, chromium oxide, navy blue, Prussian blue, carbon black and the like, the pearlescent pigment may be titanium dioxide, mica titanium, iron titanate and titanium oxide coated mica, silica, tin oxide, ferric ferrocyanide and the like, the metal powder may be gold, silver, bronze, palladium, platinum and the like, and organic powder may be polymethylmethacrylate, nylon, cellulose, starch and the like. In addition, natural, inorganic and organic pigments commonly known in the cosmetic art may be all used, and the natural pigment may be one selected from the group consisting of gardenia yellow, gardenia blue, gardenia green, gardenia red, a monascus red colorant, a monascus yellow colorant, a safflower yellow colorant, an annatto colorant, a cochineal colorant, a lac colorant, a Kaoliang colorant, a grape skin colorant, a red cabbage colorant, an elderberry colorant, a blueberry colorant, a paprika colorant, a caramel colorant, a red radish colorant, a persimmon colorant, a Jeonryuhwa colorant, riboflavin, betacarotene, a cacao colorant, a turmeric colorant, a corn red colorant, a beet red colorant, anthocyan, anthocyanin, phycocyan, phycocyanin, a chlorophyll colorant, and a combination thereof, the inorganic pigment may be one selected from the group consisting of metal oxides, in particular, iron oxides (red, black, yellow, brown), titanium dioxide, zinc oxide, chromium oxide, bismuth oxychloride, aluminum oxide, zirconium oxide, cobalt oxide, cerium oxide, nickel oxide, calcium hydroxide, iron hydroxide, aluminum hydroxide, chromium hydroxide, magnesium hydroxide, ferric ammonium ferrocyanide, Prussian blue, iron sulfide, manganese violet, carbon black, mica, kaolin, and a combination thereof, and the organic pigment may be natural or synthetic organic dyes such as indigo lake, carmine lake, well known FD&C and D&C dye series-derived lakes, for example, D&C Red 21 aluminum lake, D&C Red 7 calcium lake, aromatic azo, indigoid, triphenylmethane, anthraquinone and a xanthin dye.

The cosmetic composition of the present invention is a functional cosmetic composition for anti-aging, or a cosmetic composition for alleviation of atopic dermatitis, and depending on the administration route, it may be a composition capable of being skin-externally, transdermally or subcutaneously administered, preferably, skin-externally or transdermally, more preferably skin-externally administered, and particularly, the cosmetic composition for alleviation and treatment of atopic dermatitis is preferably a skin-external preparation.

Further, the cosmetic composition may include a solvent commonly included in an applied form, and for example, may include one or more selected from the group consisting of ethanol, glycerin, butylene glycol, propylene glycol, polyethylene glycol, 1,2,4-butanetriol, sorbitol ester, 1,2,6-hexanetriol, benzyl alcohol, isopropanol, butanediol, diethylene glycol monoethyl ether, dimethyl isosorbide, N-methyl-2-pyrrolidone, propylene carbonate, glycereth-26, methylglucese-20, isocetyl myristate, isocetyl octanoate, octyldodecyl myristate, octyldodecanol, isostearyl isostearate, cetyl octanoate, neopentylglycol dicaprate and the like. When the composition of the present invention is prepared using the solvent, the solubility of the compound to the solvent is slightly different depending on the kind of compound or a mixing ratio of solvent, however, a person skilled in the art may properly select the kind and used amount of solvent depending on the properties of the product, and apply it.

Further, the cosmetic composition may include various materials for enhancing transdermal penetration when transdermally administered. For example, it may include a laurocapram derivative and oleic acid, an ester derivative of monooleate derivative, adaphalen, tretinoin, retinaldehyde, tazarotene, salicylic acid, azelaic acid, glycolic acid, ethoxy diglycol, Tween 80, lecithin olganogel and the like. Further, in order to add an additional function to the cosmetic composition of the present invention, an auxiliary component such as a cosurfactant, a surfactant, an anti-dandruff agent, a keratin softener, a blood circulation accelerator, a cell activator, a refresher, a moisturizer, an antioxidant, a pH adjusting agent and purified water may be added, and depending on the applied form, a suitable additive such as a fragrance, a pigment, an antiseptic agent and an excipient may be contained, within the range of not inhibiting the effect of the composition of imparting the autophagy activation operational effect of the present invention.

Further, the present invention provides a food composition including the compound represented by Chemical Formula 1 or pharmaceutically acceptable salt thereof of the present invention.

The food composition of the present invention may include an acceptable food auxiliary additive, and further include suitable carrier, excipient and diluent commonly used in the preparation of functional food.

The food in the present invention refers to a natural or processed product containing one or more nutrients, preferably being in a state of being directly edible through a certain degree of processing, and in a typical sense, refers to include all various foods, health functional foods, beverages, food additives and beverage additive. As an example of the food, there are various foods, beverages, gum, tea, vitamin complexes, functional foods and the like. In addition, the food of the present invention includes special nutrition foods (e.g., modified milk, infant diet, etc.), meat products, fish products, tofu, jellied foods, noodles (e.g., ramen, noodle, etc.), health supplement food, seasoning food (e.g., soy sauce, doenjang, gochujang, mixed soy paste, etc.), sauces, confectionery (e.g., snacks), dairy products (e.g., fermented milk, cheese, etc.), other processed food, kimchi, salted foods (various kimchi, pickled vegetables, etc.), beverages (e.g., fruit drinks, vegetable drinks, soybean milk, fermented drinks, icecream, etc.), natural seasonings (e.g., ramen soup base, etc.), vitamin complexes, alcoholic beverages, alcohols and other health supplement food, but not limited thereto. The health functional food, beverages, food additives or beverage additives may be prepared in a conventional preparation method.

Further, the content of the compound represented by Chemical Formula 1 or salt thereof of the present invention included in the food composition may be 0.00001 wt % to 50 wt % based on the total weight of the food, and when the food is beverage, the compound of the present invention or the salt thereof may be contained in a ratio of 0.001 g to 50 g, preferably 0.01 g to 10 g, based on total 100 ml of the food, but not limited thereto.

Hereinafter, the present invention will be described in detail by Examples. However, the following Examples are only illustrative of the present invention, and do not limit the present invention in any way.

EXAMPLE 1

Synthesis of Compound 1

Example 1-1 Synthesis of Compound 1a

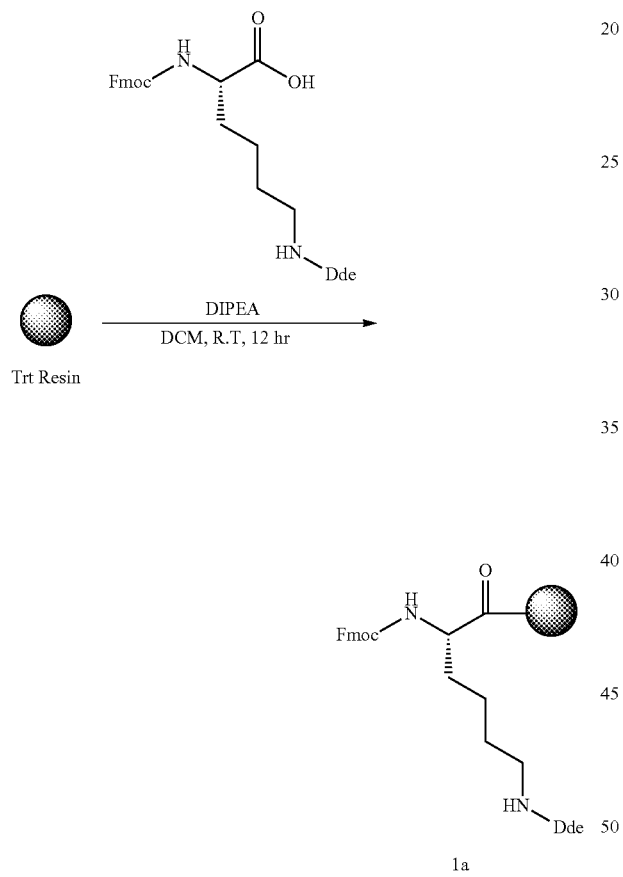

1a

Example 1-2 Synthesis of Compound 1b

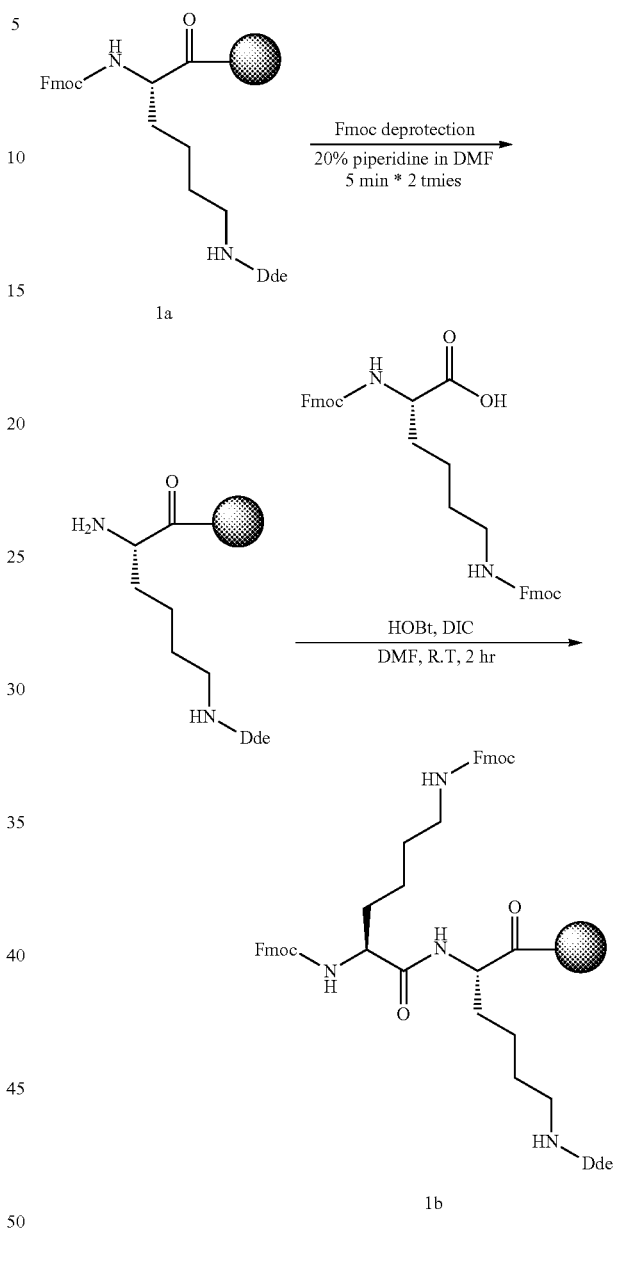

1b

Into an 800 ml reaction vessel, 2-chloro trityl chloride resin (100-200 mesh, Novabiochem, 20 g, 1 eq.), Fmoc-Lys(Dde)-OH(Nα-Fmoc-Nε-Dde-L-lysine,Nα-Fmoc-Nε-[1-(4,4-dimethyl-2,6-dioxocyclohexylidene)ethyl]-L-lysine) (21.3 g, 2 eq.), and DIPEA (29.9 ml, 8 eq.) were added together with DCM (700 ml), and reacted at room temperature for 12 hours. The reaction solution was removed by filtering, and the synthesized resin was sequentially washed using 500 ml of each of DCM (dichloromethane) and MeOH, DCM, and DMF (dimethylformamide). Vacuum drying was carried out to obtain 23 g of Compound 1a (Fmoc-Lys(Dde)-O-2-chloro trityl resin) in a solid phase form at a yield of 99%.

Into an 800 ml reaction vessel, Compound 1a and 700 ml of 20% piperidine in DMF were added, reacted at room temperature for 5 minutes, and filtered to remove the reaction solution. 700 ml of 20% piperidine in DMF was added once more, and reacted at room temperature for 5 minutes. The reaction solution was removed by filtering, and the synthesized resin was sequentially washed using 500 ml of each of DCM, MeOH, DCM and DMF. To the product from which Fmoc in a solid phase form was removed by vacuum drying, Fmoc-Lys(Fmoc)-OH (47.3 g, 4 eq.), HOBt (10.8 g, 4 eq.) and DIC (12.4 ml, 4 eq.) dissolved in 600 ml of DMF were added, and reacted at room temperature for 4 hours. The reaction solution was removed by filtering, and the synthesized resin was sequentially washed using 500 ml of each of DCM and MeOH, DCM, and DMF. Vacuum drying was carried out to obtain 25 g of Compound 1b (Fmoc-Lys (Fmoc)-Lys(Dde)-O-2-chloro trityl resin) in a solid phase form at a yield of 98%.

Example 1-3 Synthesis of Compound 1c

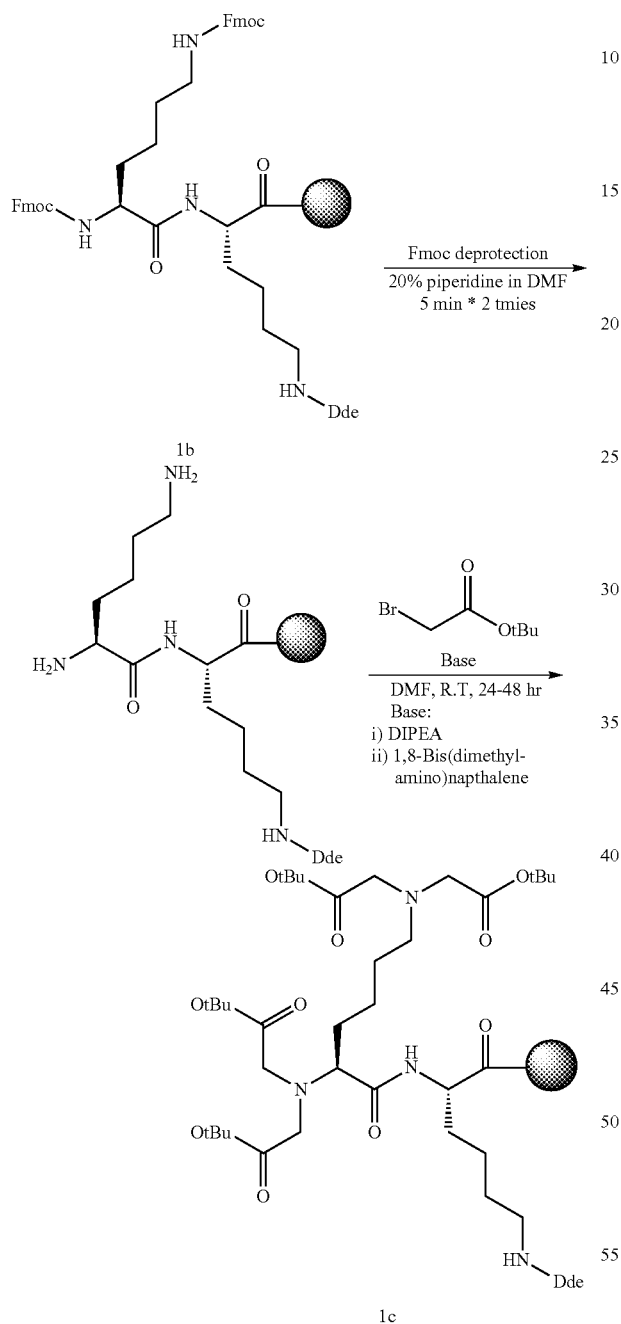

Into an 800 ml reaction vessel, Compound 1b and 700 ml of 20% piperidine in DMF were added, reacted at room temperature for 5 minutes, and filtered to remove the reaction solution. 700 ml of 20% piperidine in DMF was added once more, and reacted at room temperature for 5 minutes. The reaction solution was removed by filtering, and the synthesized resin was sequentially washed using 500 ml of each of DCM and MeOH, DCM, and DMF. To the product from which Fmoc in a solid phase form was removed by vacuum drying, tert-butyl bromoacetate (59.1 ml, 20 eq.) and DIPEA (69.7 ml, 20 eq.) dissolved in 600 ml of DMF were added, and reacted at room temperature for 12 hours. The reaction solution was removed by filtering, and the synthesized resin was washed using 500 ml of DMF. Again, 1,8-Bis(dimethylamino)naphthalene (85.7 g, 20 eq.), tert-butyl bromoacetate (59.1 ml, 20 eq.), and DIPEA (69.7 ml, 20 eq.) dissolved in 600 ml of DMF were added thereto, and reacted at room temperature for 12 hours. The reaction solution was removed by filtering, and the synthesized resin was sequentially washed using 500 ml of each of DCM and MeOH, DCM, and DMF. Vacuum drying was carried out to obtain 31 g of Compound 1c (tert-butoxycarbonylmethyl) 2-Lys(tert-butoxycarbonylmethyl)2-Lys(Dde)-O-2-chloro trityl resin) in a solid phase form at a yield of 95%.

Example 1-4 Synthesis of Compound 1d

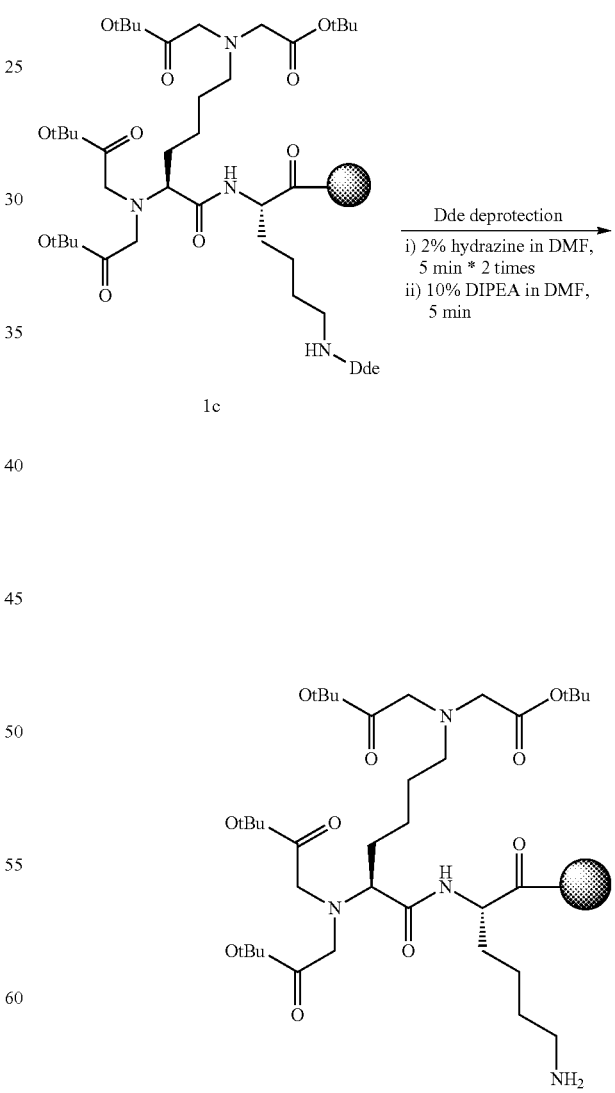

Into an 800 ml reaction vessel, Compound 1c and 700 ml of 2% hydrazine in DMF were added, and reacted at room temperature for 5 minutes. The reaction solution was removed by filtering, and the synthesized resin was washed using 500 ml of DMF. Again, 700 ml of 10% DIPEA in DMF was added thereto once more, and reacted at room temperature for 5 minutes. The reaction solution was removed by filtering, and the synthesized resin was sequentially washed using 500 ml of each of DCM and MeOH, DCM, and DMF. Vacuum drying was carried out to obtain 30 g of Compound 1d (tert-butoxycarbonylmethyl)2-Lys(tert-butoxycarbonylmethyl)2-Lys(NH2)-O-2-chloro trityl resin) in a solid phase form at a yield of 99%.

Example 1-5 Synthesis of Compound 1 by Removal Reaction of Resin and Protection Group

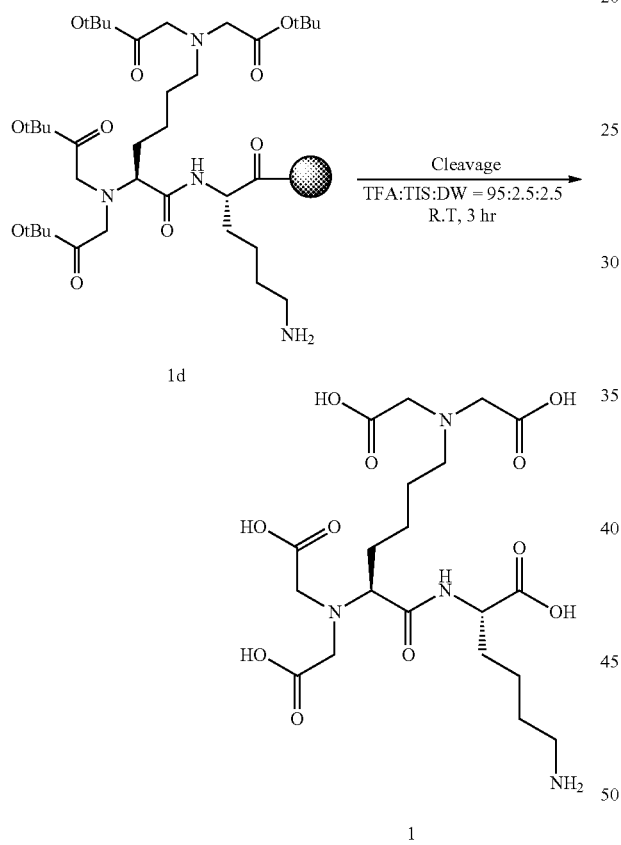

Into a 10 ml reaction vessel, Compound 1d (1 g, 1 eq.) was added, 5 ml of a cleavage cocktail (trifluoro acetic acid:triisopropylsilane:DW=95:2.5:2.5) was added, and reacted at room temperature for 3 hours. Filtering was carried out to collect the reaction solution, and 45 ml of diethyl ether was added thereto to precipitate the product. The solid product was collected using a centrifuge, and washed twice with 45 ml of diethyl ether. The obtained solid product was purified using Prep-HPLC (column C18, 10 um, 250 mm×22 mm), and then lyophilized to obtain 181 mg of Compound 1 (molecular weight measured by LC mass: 506.5) at a yield of 77%.

EXAMPLE 2

Synthesis of Compound 2

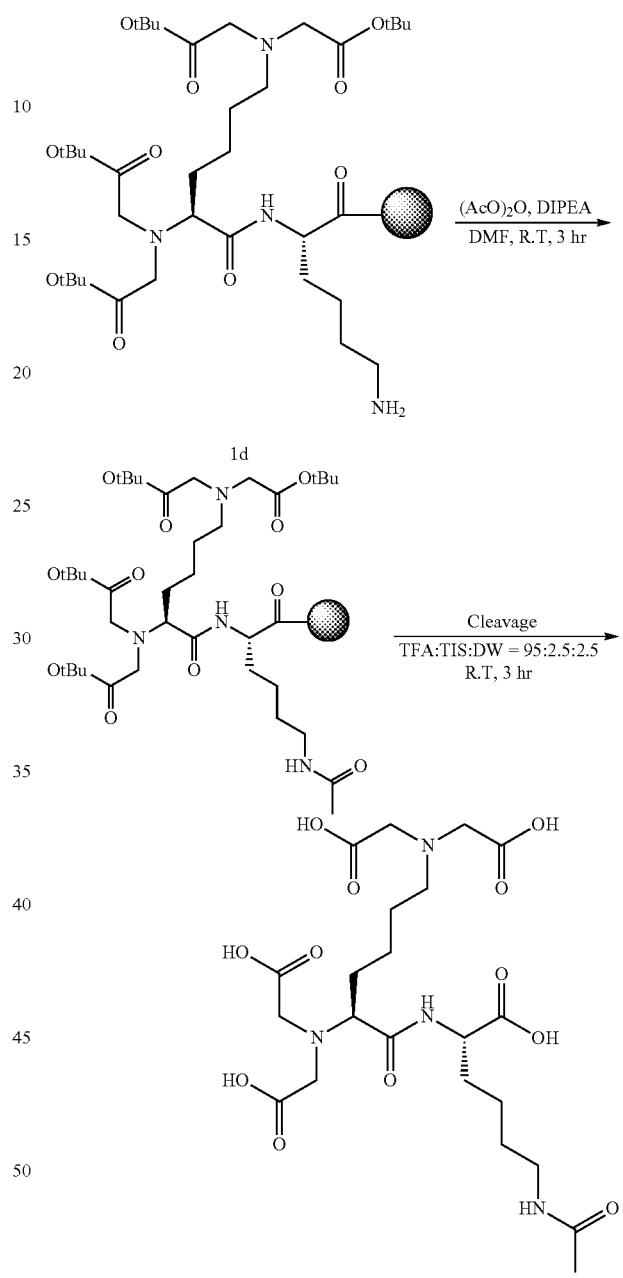

Into a 10 ml reaction vessel, Compound 1d (460 mg, 1 eq.) was added, acetic anhydride (200 ul, 8 eq.) and DIPEA (200 ul, 8 eq.) dissolved in 5 ml of DMF were added thereto, and reacted at room temperature for 30 minutes. The reaction solution was removed by filtering, and the synthesized resin was sequentially washed using 5 ml of each of DCM and MeOH, and DCM. After vacuum drying, 5 ml of a cleavage cocktail (trifluoro acetic acid:triisopropylsilane: DW=95:2.5:2.5) was added thereto, and reacted at room temperature for 3 hours. Filtering was carried out to collect the reaction solution, and 45 ml of diethyl ether was added thereto to precipitate the product. The solid product was collected using a centrifuge, and washed twice with 45 ml of diethyl ether. The obtained solid product was purified using Prep-HPLC (column C18, 10 um, 250 mm×22 mm), and then lyophilized to obtain 80 mg of Compound 2 (molecular weight measured by LC mass: 548.54) at a yield of 66%.

EXAMPLE 3

Synthesis of Compound 3

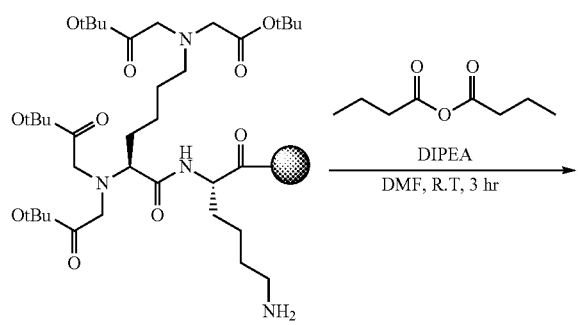

Into a 10 ml reaction vessel, Compound 1d (460 mg, 1 eq.) was added, butyric anhydride (200 ul, 8 eq.) and DIPEA (200 ul, 8 eq.) dissolved in 5 ml of DMF were added thereto, and reacted at room temperature for 1 hour. The reaction solution was removed by filtering, and the synthesized resin was sequentially washed using 5 ml of each of DCM and MeOH, and DCM. After vacuum drying, 5 ml of a cleavage cocktail (trifluoro acetic acid:triisopropylsilane:DW=95:2.5:2.5) was added thereto, and reacted at room temperature for 3 hours. Filtering was carried out to collect the reaction solution, and 45 ml of diethyl ether was added thereto to precipitate the product. The solid product was collected using a centrifuge, and washed twice with 45 ml of diethyl ether. The obtained solid product was purified using Prep-HPLC (column C18, 10 um, 250 mm×22 mm), and then lyophilized to obtain 75 mg of Compound 3 (molecular weight measured by LC mass: 576.59) at a yield of 68%.

EXAMPLE 4

Synthesis of Compound 4

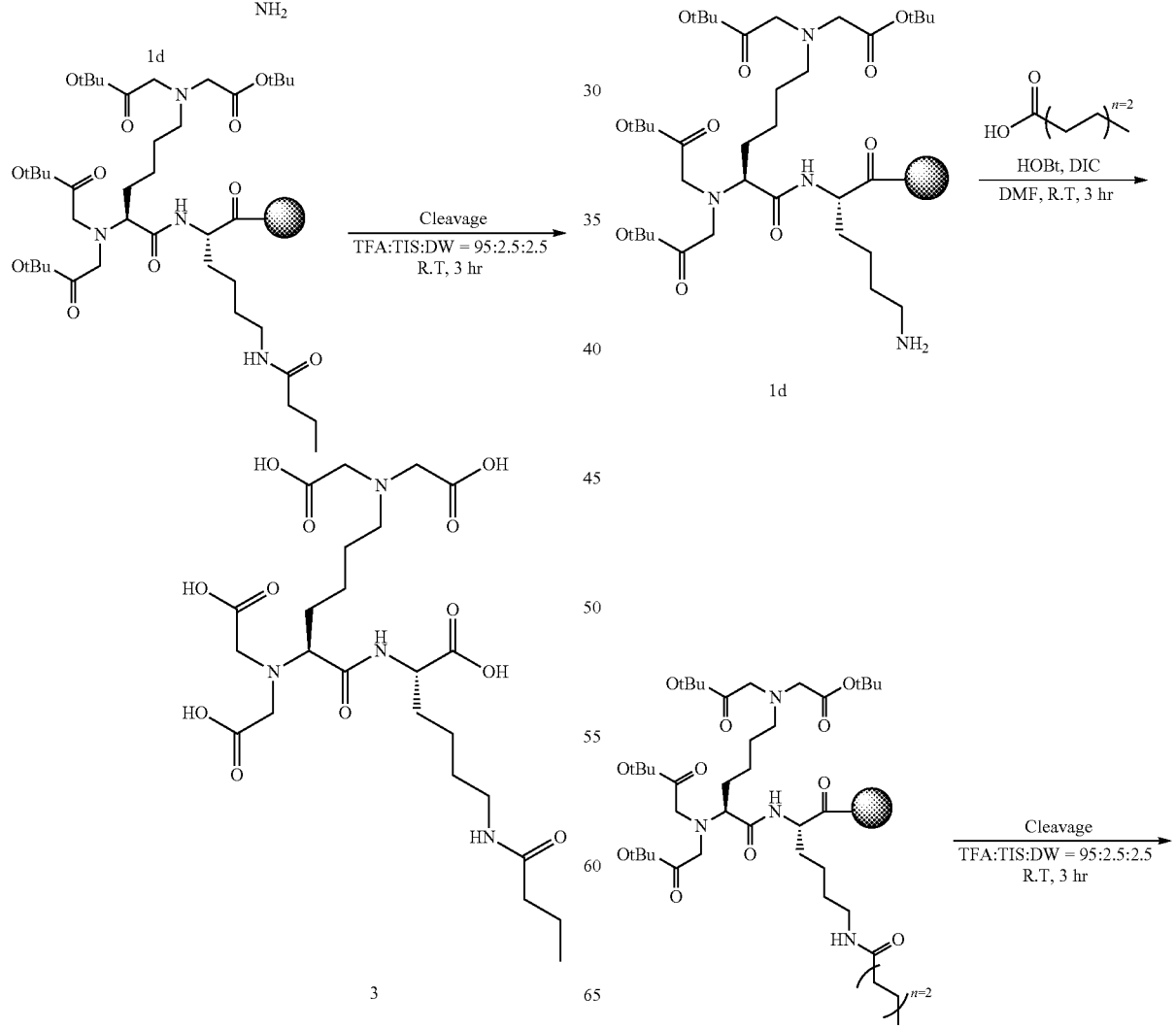

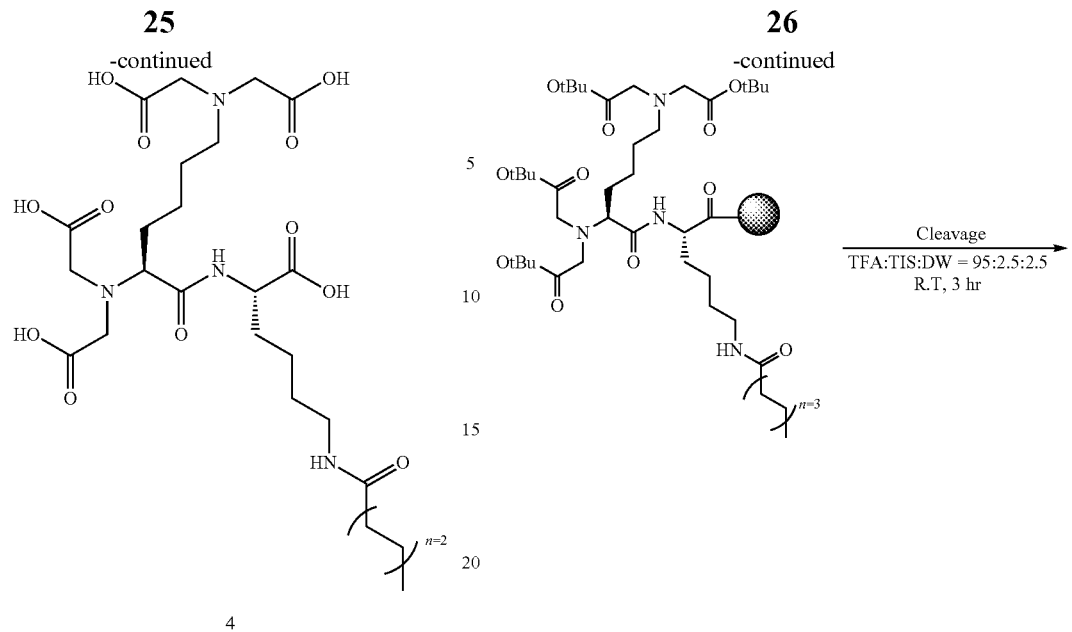

Into a 10 ml reaction vessel, Compound 1d (460 mg, 1 eq.) was added, hexanoic acid (186 ul, 8 eq.), DIC (248 ul, 8 eq.), and HOBt (216 mg, 8 eq.) dissolved in 5 ml of DMF were added thereto, and reacted at room temperature for 2 hours. The reaction solution was removed by filtering, and the synthesized resin was sequentially washed using 5 ml of each of DCM and MeOH, and DCM. After vacuum drying, 5 ml of a cleavage cocktail (trifluoro acetic acid:triisopropylsilane:DW=95:2.5:2.5) was added thereto, and reacted at room temperature for 3 hours. Filtering was carried out to collect the reaction solution, and 45 ml of diethyl ether was added thereto to precipitate the product. The solid product was collected using a centrifuge, and washed twice with 45 ml of diethyl ether. The obtained solid product was purified using Prep-HPLC (column C18, 10 um, 250 mm×22 mm), and then lyophilized to obtain 77 mg of Compound 4 (molecular weight measured by LC mass: 604.65) at a yield of 64%.

EXAMPLE 5

Synthesis of Compound 5

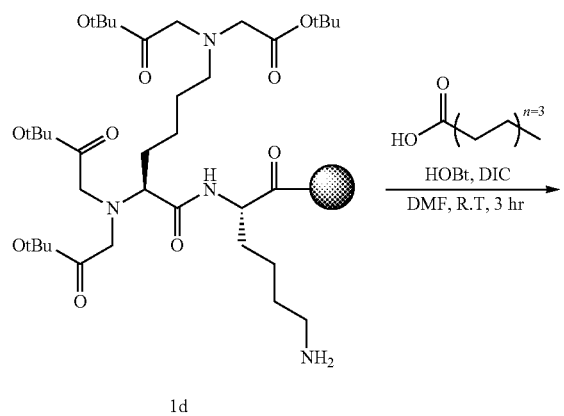

Into a 10 ml reaction vessel, Compound 1d (460 mg, 1 eq.) was added, octanoic acid (230 ul, 8 eq.), DIC (248 ul, 8 eq.), and HOBt (216 mg, 8 eq.) dissolved in 5 ml of DMF were added thereto, and reacted at room temperature for 2 hours. The reaction solution was removed by filtering, and the synthesized resin was sequentially washed using 5 ml of each of DCM and MeOH, and DCM. After vacuum drying, 5 ml of a cleavage cocktail (trifluoro acetic acid:triisopropylsilane:DW=95:2.5:2.5) was added thereto, and reacted at room temperature for 3 hours. Filtering was carried out to collect the reaction solution, and 45 ml of diethyl ether was added thereto to precipitate the product. The solid product was collected using a centrifuge, and washed twice with 45 ml of diethyl ether. The obtained solid product was purified using Prep-HPLC (column C18, 10 um, 250 mm×22 mm), and then lyophilized to obtain 62 mg of Compound 5 (molecular weight measured by LC mass: 632.7) at a yield of 56%.

EXAMPLE 6

Synthesis of Compound 6

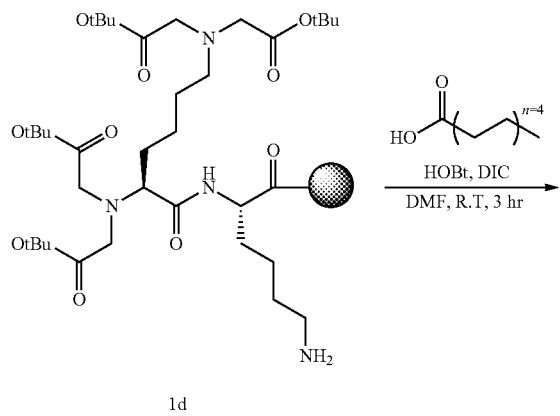

Into a 10 ml reaction vessel, Compound 1d (460 mg, 1 eq.) was added, decanoic acid (275 ul, 8 eq.), DIC (248 ul, 8 eq.), and HOBt (216 mg, 8 eq.) dissolved in 5 ml of DMF were added thereto, and reacted at room temperature for 2 hours. The reaction solution was removed by filtering, and the synthesized resin was sequentially washed using 5 ml of each of DCM and MeOH, and DCM. After vacuum drying, 5 ml of a cleavage cocktail (trifluoro acetic acid:triisopropylsilane:DW=95:2.5:2.5) was added thereto, and reacted at room temperature for 3 hours. Filtering was carried out to collect the reaction solution, and 45 ml of diethyl ether was added thereto to precipitate the product. The solid product was collected using a centrifuge, and washed twice with 45 ml of diethyl ether. The obtained solid product was purified using Prep-HPLC (column C18, 10 um, 250 mm×22 mm), and then lyophilized to obtain 79 mg of Compound 6 (molecular weight measured by LC mass: 660.36) at a yield of 66%.

EXAMPLE 7

Synthesis of Compound 7

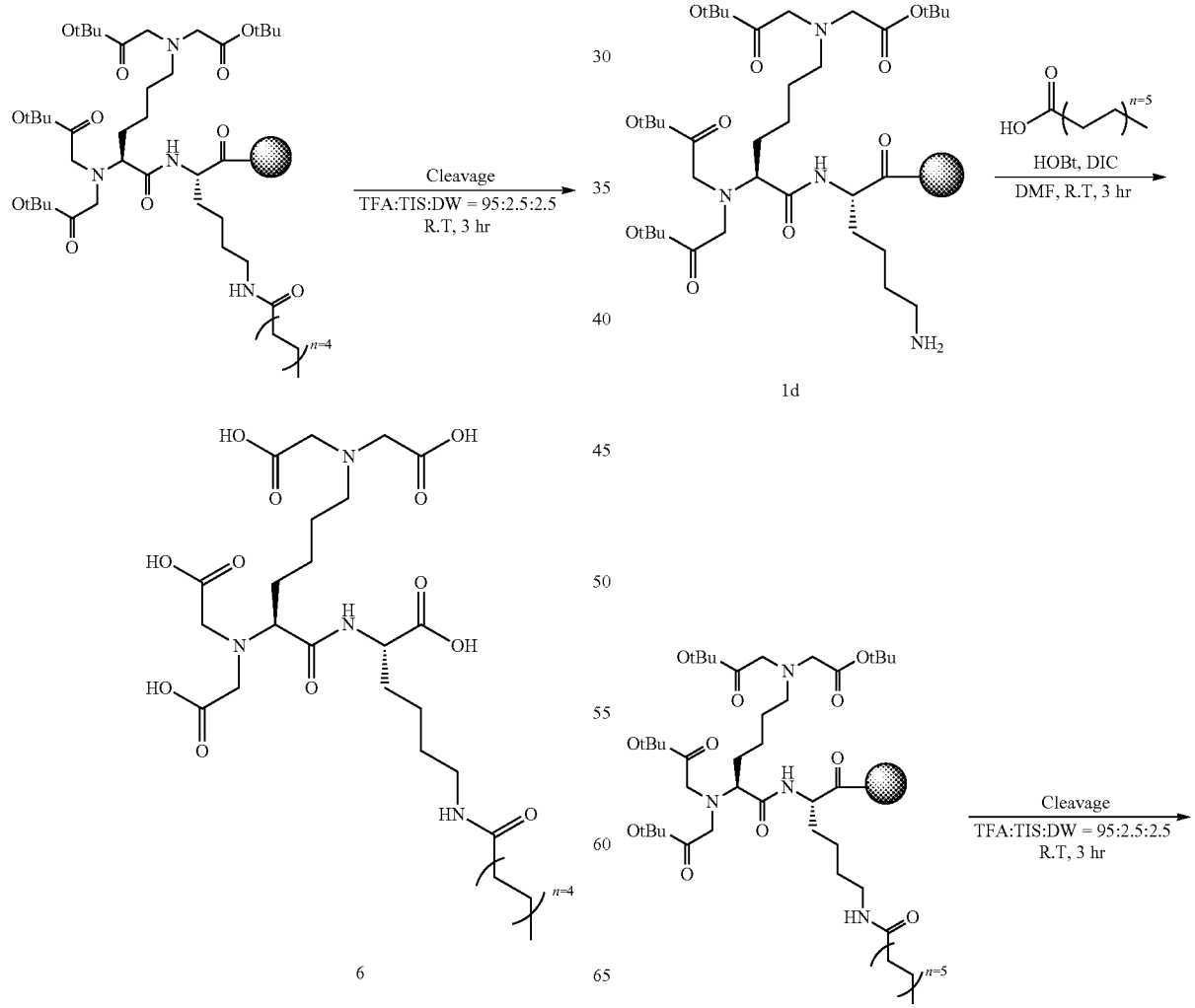

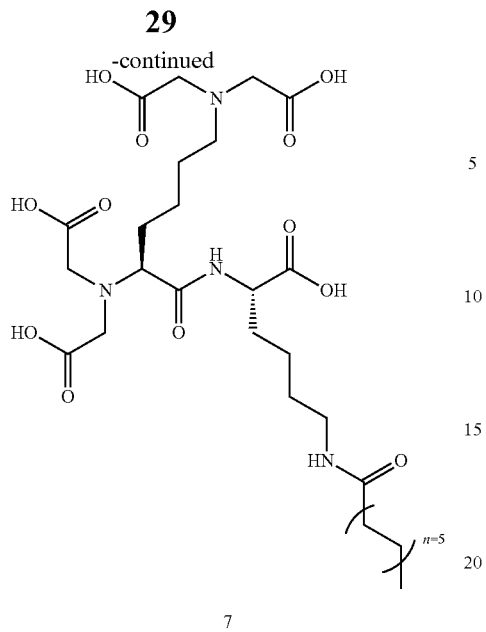

7

Into a 10 ml reaction vessel, Compound 1d (460 mg, 1 eq.) was added, dodecanoic acid (320 ul, 8 eq.), DIC (248 ul, 8 eq.), and HOBt (216 mg, 8 eq.) dissolved in 5 ml of DMF were added thereto, and reacted at room temperature for 2 hours. The reaction solution was removed by filtering, and the synthesized resin was sequentially washed using 5 ml of each of DCM and MeOH, and DCM. After vacuum drying, ml of a cleavage cocktail (trifluoro acetic acid:triisopropyl-silane:DW=95:2.5:2.5) was added thereto, and reacted at room temperature for 3 hours. Filtering was carried out to collect the reaction solution, and 45 ml of diethyl ether was added thereto to precipitate the product. The solid product was collected using a centrifuge, and washed twice with 45 ml of diethyl ether. The obtained solid product was purified using Prep-HPLC (column C18, 10 um, 250 mm×22 mm), and then lyophilized to obtain 72 mg of Compound 7 (molecular weight measured by LC mass: 688.81) at a yield of 62%.

EXAMPLE 8

Synthesis of Compound 8

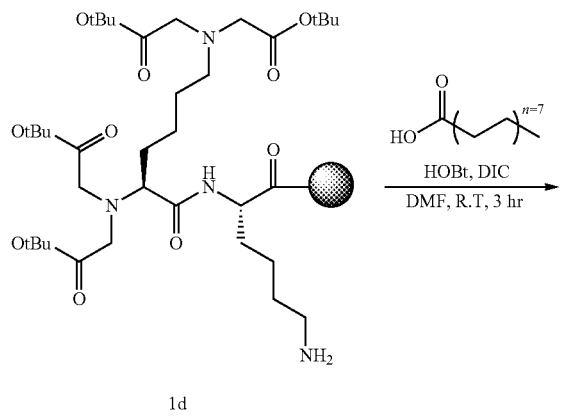

1d

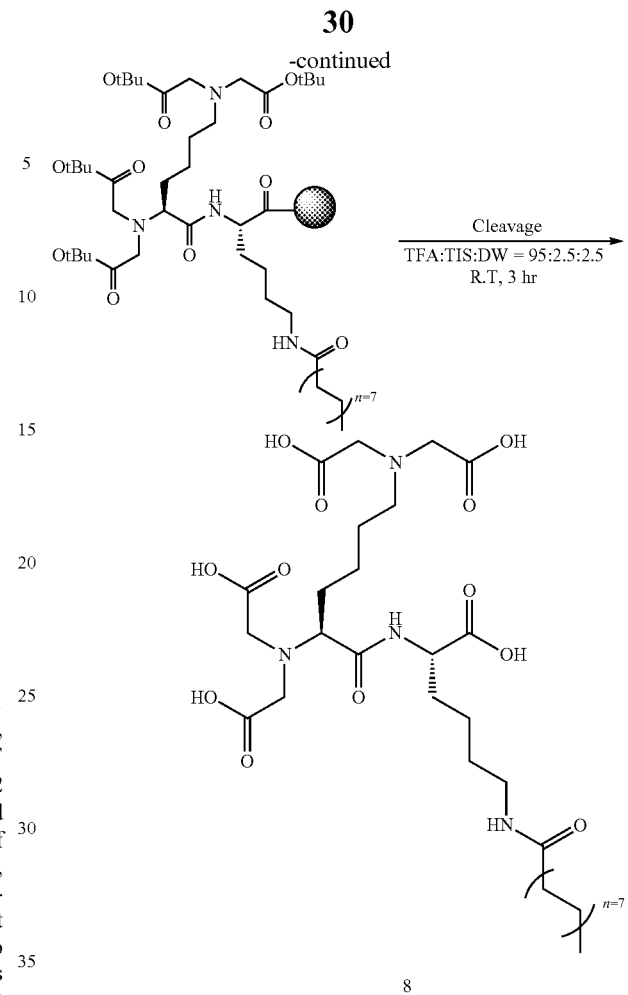

8

Into a 10 ml reaction vessel, Compound 1d (460 mg, 1 eq.) was added, palmitic acid (308 mg, 8 eq.), DIC (248 ul, 8 eq.), and HOBt (216 mg, 8 eq.) dissolved in 5 ml of DMF were added thereto, and reacted at room temperature for 3 hours. The reaction solution was removed by filtering, and the synthesized resin was sequentially washed using 5 ml of each of DCM and MeOH, and DCM. After vacuum drying, 5 ml of a cleavage cocktail (trifluoro acetic acid:triisopropylsilane:DW=95:2.5:2.5) was added thereto, and reacted at room temperature for 3 hours. Filtering was carried out to collect the reaction solution, and 45 ml of diethyl ether was added thereto to precipitate the product. The solid product was collected using a centrifuge, and washed twice with 45 ml of diethyl ether. The obtained solid product was purified using Prep-HPLC (column C18, 10 um, 250 mm×22 mm), and then lyophilized to obtain 80 mg of Compound 8 (molecular weight measured by LC mass: 744.93) at a yield of 70%.

EXAMPLE 9

Increased Autophagy Activation By Compound 8 of The Present Invention

In order to analyze increased intracellular autophagy activation by treatment of Compound 8 of the present invention, a western blot analysis for LC3 (light chain 3) protein was performed.

As a specific experimental method, HaCaT, human epidermal keratinocytes were seeded in on a 6 well plate at a density of 3×10⁵ cells, and cultured in DMEM (Dulbecco's Modified Eagle Media, Gibco BRL) in an incubator under 37° C. and 5% $CO_2$ for 24 hours. Compound 8 of the present invention was dissolved in DMSO at a concentration of 10 mM to be a concentrate, and diluted with a medium to be at a concentration of 20 uM. Then in a state where 1 ml of medium was first in each well, 1 ml of each diluted solution was added thereto for treatment, and cultured for a certain period, and after completing the culture, the medium was removed, and then cells were disrupted with a SDS sample buffer, and each protein was separated by SDS-PAGE gel electrophoresis, and transferred to a PVDF (polyvinylidene fluoride) membrane. Thereafter, non-specific binding was eliminated using a blocking buffer, and an antibody against LC3 protein and a HRP-bound secondary antibody (anti-rabbit IgG HRP (sigma)) were reacted, and then an enhanced chemiluminescence (ECL) reaction using an ECL prime kit (Amersham Pharmacia) was carried out, thereby performing a ChemiDoc analysis.

As shown in FIG. 1 representing the result, it was recognized that production of LC3-II (Microtubule-associated protein 1A/1B-light chain 3) was increased in Compound 8 of the present invention.

EXAMPLE 10

Autophagy Activation Protein Regulation by Compound 8 of The Present Invention

In order to analyze which gene expression is related to increased autophagy activation by Compound 8 of the present invention, a western blot analysis for Beclin-1 and ULK-1 (Serine/threonine-protein kinase-1) proteins which are closely related to autophagy activation was performed.

As a specific experimental method, HaCaT cells, human-derived keratinocytes were seeded on a 60Ø dish at a density of 3×10⁵ cells, and cultured in DMEM (Dulbecco's Modified Eagle Media, Gibco BRL) in an incubator under 37° C. and 5% $CO_2$ for 24 hours. Compound 8 of the present invention was dissolved in DMSO at a concentration of 10 mM each to be a concentrate, and diluted with a medium to be at a concentration of 20 uM. Then in a state where 1 ml of medium was first in each well, 1 ml of each diluted solution was added thereto for treatment, and cultured for a certain period, and after completing the culturing, the medium was removed, and then cells were disrupted with a SDS sample buffer, and each protein was separated by SDS-PAGE gel electrophoresis, and transferred to a PVDF membrane. Thereafter, non-specific binding was eliminated using a blocking buffer, and an antibodies against Beclin-1 and Ulk-1 proteins and a HRP-bound secondary antibody (anti-rabbit IgG HRP (sigma)) were reacted, and then an enhanced chemiluminescence (ECL) reaction using an ECL prime kit (Amersham Pharmacia) was carried out, thereby performing a ChemiDoc analysis.

The result is shown in FIG. 1, and as recognized from FIG. 1, in the case of treatment with Compound 8 of the present invention, the expression of Beclin-1 and ULK-1 proteins which are genes highly related to autophagy activation was significantly increased.

EXAMPLE 11

Psoriasis Alleviation Effect by Compound 8 of The Present Invention

A psoriasis-related genes were selected from the cDNA array result in which Compound 8 of the present invention was treated in HaCaT cells. In order to analyze whether Compound 8 has an effect on psoriasis alleviation, RT-PCR analysis for IL-36' (interleukin 36 gamma), KLK7 (Kallikrein-related peptidase 7), OASL (2'-5'-Oligoadenylate Synthetase Like) and ALOX12B (Arachidonate 12-lipoxygenase, 12R type) which are very closely related to psoriasis was carried out. Further, KRT16 (Keratin 16), KRT6 (Keratin 6) and KRT1 (Keratin 1), known as psoriasis-related proliferation, differentiation markers were confirmed by a western blot analysis. As the specific experimental method, HEKa cells (Human Epidermal keratinocytes, adult), human-derived epidermal keratinocytes were seeded on a 24 well plate at a density of 1×10⁵ cells, and cultured in an EpiLife medium (1× Human keratinocyte Growth supplement, 1× antibiotics) in an incubator under 37° C. and 5% $CO_2$ for 24 hours. Compound 8 of the present invention was dissolved in DMSO at a concentration of 10 mM to be a concentrate, dissolved in a medium to be concentrated at a concentration of 20 uM, and then 1 ml of each diluted solution was added thereto for treatment, and then cultured for a certain period, and after completing culturing, cells were disrupted with Trizol (Life Science), and total mRNA was collected with chloroform/isopropanol, and then cDNA was synthesized with reverse-transcriptase, and PCR was performed using a specific primer for each gene. PCR products were analyzed with agarose gel electrophoresis, and the result is shown in FIG. 2.

As shown in FIGS. 2 and 3, it was confirmed that when treating Compound 8 of the present invention, expression levels of IL-36G (interleukin 36, gamma), KLK7 (Kallikrein-related peptidase 7), OASL (2'-5'-Oligoadenylate Synthetase Like) and ALOX12B (Arachidonate 12-lipoxygenase, 12R type) genes which are highly related to psoriasis were significantly decreased. In addition, (, it was confirmed that the expression levels of Tbet (T-box transcription factor), STAT3 (Signal transducer and activator of transcription 3), and Foxp3 (forkhead box P3) which are transcription factors related to psoriasis were reduced by Compound 8 treatment in IL-17A (interleukin-17A)/TNFα (Tumor necrosis factor alpha)- or IL-17A/IFNγ (interferon gamma)-induced inflammatory condition. In FIG. 4, it was confirmed that KRT6 (Keratin 6) and KRT16 (Keratin 16) which are proliferative markers were reduced, and KRT1 (Keratin 1) which is a differentiation marker was increased by Compound 8 treatment.

EXAMPLE 12

Anti-atopy and Psoriasis Alleviation Effect by Compound 8 of The Present Invention In order to analyze whether treatment of Compound 8 has an atopy alleviation effect, ELISA (enzyme-linked immunosorbent assay) for IL-6 (interleukin 6) and IL-8 (interleukin 8) which are very closely related to atopic inflammation and psoriasis was performed.

As the specific experimental method, HEKa cells (Human Epidermal keratinocytes, adult), human-derived epidermal keratinocytes were seeded on a 24 well plate at a density of 1×10⁵ cells, and cultured in an EpiLife medium (1× Human keratinocyte Growth supplement, 1× antibiotics) in an incubator under 37° C. and 5% $CO_2$ for 24 hours.

After culturing, while an inflammatory condition was induced by treatment with either TNF-α (Tumor necrosis factor-α)/IFN-γ (interferon-γ) or IL-17A (interleukin-17A)/IL-22 (interleukin-22) in each well, further treatment was performed with Compound 8 of the present invention at a concentration of 10·M, and then the cells were incubated for a certain period. After completing culturing, media were collected, and then ELISA for each IL-6 and IL-8 was carried out. As shown in FIGS. 5 to 7, the secretion of IL-6 and IL-8 was significantly reduced by Compound 8 of the present invention.

As shown in FIG. 8, it was confirmed that in the case of treatment with Compound 8 of the present invention, the expression levels of IL-24 (interleukin-24), IL-20 (interleukin-20) and CXCL2 (Chemokine (C-X-C motif) ligand 2) in TNFα/IFN-γ induced inflammatory condition were reduced by Compound 8. In addition, as shown in FIG. 9, it was confirmed that the expression levels of IL-8 (interleukin-8), IL-36γ (interleukin 36, gamma) and CCL20 (Chemokine (C-C motif) ligand 20) in IL-17A/TNF-α were reduced by Compound 8.

Thus, it is recognized that the compound of Chemical Formula 1 which is the autophagy activation-inducing compound of the present invention may be used in alleviation, treatment and prevention of atopy dermatitis and psoriasis very effectively.

EXAMPLE 13 AND COMPARATIVE EXAMPLE 1

Anti-atopy And Psoriasis Alleviation Effect by Compound 8 of The Present Invention ELISA (enzyme-linked immunosorbent assay) for IL-1β (interleukin-1beta) which is very closely related to atopic inflammation and psoriasis was performed.

As a specific experimental method, HEKa cells (Human Epidermal keratinocytes, adult), human-derived epidermal keratinocytes were seeded on a 24 well plate at a density of $1 \times 10^5$ cells, and cultured in an EpiLife medium (1× Human keratinocyte Growth supplement, 1× antibiotics) in an incubator under 37° C. and 5% $CO_2$ for 24 hours.

After culturing, while an inflammatory condition was induced by treatment with LPS (lipopolysaccharides) in each well, further treatment was performed with Compound 8 of the present invention and the compound of the following Comparative Example at a concentration of 10·M, and then the cells were incubated for a certain period. After completing culturing, media were collected, and then ELISA for IL-1β was carried out, and the results are shown in FIG. 10.

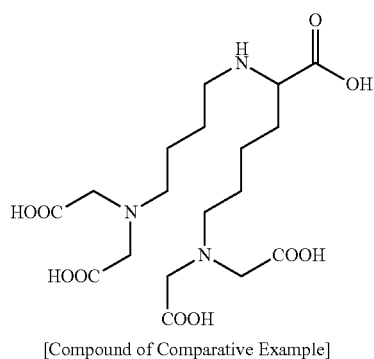 [SMILES: O=C(O)CN(CCCCNC(CCCCN(CC(=O)O)CC(=O)O)C(=O)O)CC(=O)O]

[Compound of Comparative Example]

As shown in FIG. 10, it is recognized that cytokine IL-1β secretion level was significantly reduced by Compound 8 which is the autophagy activation-inducing compound of the present invention, whereas in the case of treatment with the compound of the Comparative Example, the reduction effect of cytokine IL-1β was negligible.

EXAMPLE 14 AND COMPARATIVE EXAMPLE 2

Cosmetic Composition Including Compound 8 of The Present Invention

Cosmetic compositions including Compound 8 prepared in Example 8 of the present invention were prepared with the components and the contents listed in Table 1.

Compound 8 of the present invention, a carboxyvinyl polymer, butylene glycol and glycerin were stirred with mixing in purified water, while heated to 80° C., and added to an emulsification reactor, and all components except triethanolamine were added thereto and heated to 80° C. to be emulsified. Thereafter, when emulsification was completed, stirring was carried out with a stirrer and cooling to room temperature was carried out, thereby preparing cosmetic compositions.

TABLE 1

| Components | Contents of Example 14 (wt %) | Contents of Comparative Example 2 (wt %) |
|---|---|---|
| Compound 8 of the present invention | 4.0 | — |
| Stearic acid | 3.0 | 3.0 |
| Cetyl alcohol | 3.0 | 3.0 |
| Sorbitan sesquioleate | 0.5 | 0.5 |
| Glyceryl monostearate | 0.5 | 0.5 |
| Polyoxyethylene sorbitan monostearate | 0.5 | 0.5 |
| Carboxyvinyl polymer | 0.2 | 0.2 |
| Butylene glycol | 5.0 | 5.0 |
| Squalane | 5.0 | 5.0 |
| Wax | 5.0 | 5.0 |
| Liquid paraffin | 5.0 | 5.0 |
| Glycerin | 4.0 | 4.0 |
| Glyceryl monostearate/glyceryl stearate/Polyoxyethylene stearate | 2.0 | 2.0 |
| Triethanolamine | 0.5 | 0.5 |
| Purified water | Residual amount | Residual amount |

In order to confirm an alleviation effect of atopic dermatitis and psoriasis of the cosmetic compositions of Example 14 and Comparative Example 2 as prepared, the cosmetic compositions of Example 14 of the present invention and Comparative Example 2 were provided for 20 subjects in their 10 s to 60 s having atopy and psoriasis symptoms (itching, erosion or severe dryness), who applied the composition on the area showing atopy and psoriasis symptoms twice a day for 12 weeks. After treatment for 12 weeks, the improvement degrees of atopy and psoriasis symptoms were investigated through a survey. The survey was for improvement degree of representative atopic or psoriasis dermatitis symptoms such as "itching", "dryness", "keratinization", "dandruff", "erythema", "swelling", "skin crack" and "oozing and eczema". In the case of having the symptoms, the subjects evaluated the improvement degree of each symptom, and then the degrees were averaged, thereby evaluating overall improvement degree of atopic or psoriasis dermatitis of each subject, and the number of subject for each improvement degree is shown in Table 2.

TABLE 2

| | Number of subjects for each degree | | | |
|---|---|---|---|---|
| | Significantly improved | Improved | No change | Worse |
| Example 14 | 6 | 3 | 1 | 0 |
| Comparative Example 2 | 0 | 2 | 7 | 1 |

As seen from Table 2, it is recognized that the atopy and psoriasis symptoms of the group applying the cosmetic composition including the autophagy activation-inducing compound of the present invention applied thereon were significantly improved.

Hereinafter, in order to confirm that Compound 8 of the present invention is effective in psoriasis treatment, a psoriasis animal model was prepared to carry out an experiment, and the experiment method is as follows:

[Preparation Method of Psoriasis Animal Model]

In order to confirm the psoriasis treatment effect by Compound 8 of the present invention, dorsal hair of 8-week-old BALB/c mice (female) was removed using hair removal cream (Veet®, Oxy Reckitt Benckiser, Cedex, France), and subsequently imiquimod 5% cream (Aldara®; 3M Pharmaceuticals, UK; 62.5 mg) was applied on the back and both ears of the mice twice in the morning and in the afternoon (Sensitization; Day 0). Then, after a barrier recovery period of 2 days, imiquimod 5% cream (62.5 mg/day) was applied repeatedly for 7 days (Induction stage; Day 2 -Day 8), thereby inducing the psoriasis animal model.

[Treatment Method with Compound 8 of the Present Invention on Back of Psoriasis Animal Model]

After inducing the psoriasis animal model, Compound 8 of the present invention dissolved in ethanol (0.5%) and cream containing Compound 8 of the present invention (The same composition as that of the cosmetic composition of Example 14 except that it contained 0.5% by weight of Compound 8) were applied on the back once in the morning for 5 days (Treatment Stage; Day 8-Day 12). An untreated control group and a disease control group (vehicle) were treated with cream not containing Compound 8 of the present invention (cosmetic composition of Comparative Example 2) and ethanol, and during the treatment period, imiquimod 5% cream was applied thereon every other day, thereby maintaining psoriasis. Animal slaughter was performed on the afternoon of Day 12, and such method is shown in FIG. 11.

[Treatment Method with Compound 8 of the Present Invention on Ears of Psoriasis Animal Model]

The treatment of mice ears with the compound 8 of the present invention was carried out on the 8th day after sensitization and continued for 6 consecutive days, as suggested above. There was no treatment on the left ear of the untreated control group, and the right ear was treated with cream not containing imiquimod and ethanol. The left ear of the experimental groups was treated only with imiquimod and ethanol, whereas the right ear of the experimental groups was treated with either Compound 8 or Compound 8 cream of the present invention together with imiquimod, and such method is specifically shown in FIG. 12.

[Measurement of Transepidermal Water Loss (TEWL)]

Before slaughter of the experimental animals (Days 0, 8, 11, and 14), the animals were left in space where constant temperature/constant humidity is maintained for 30 minutes, and then the probe of a corneometer was brought into close contact with the skin surface on the left and right sides of the back and lightly pressed thereon, thereby recording the appeared numerical value.

[Measurement of Ear Thickness of Animal]

When the animals were slaughtered, the thickness of the central part of both ears was measured using a digital caliper (Digital caliper, Marathon Inc. Belleville, ON, Canada).

[Hematoxylin & Eosin (H&E) Staining]

The back tissue of the experimental animal (2 cm×2 cm) was fixed in 4% paraformaldehyde for 1 day, and then embedded with paraffin. After embedding, the tissue was sectioned at a thickness of 5 μm using a microtome (Leica RM 2235, Leica Biosystems Inc. Buffalo Grove, Ill., USA), and universal H&E (Hematoxylin & Eosin) staining (Jonathan M. S. et al., J. Clin. Invest. 101, 1614-1622, 1998) was performed. Thereafter, photographs of three random parts per each tissue were taken using a microscope.

EXAMPLE 15

Effect of Treatment With Compound 8 of The Present Invention on Clinical and Histological Findings of Psoriasis The clinical changes (FIGS. 13 and 14) and histological changes (FIG. 15) of psoriasis like skin lesion such as erythema and increased thickness of stratum corneum were confirmed in the psoriasis animal group (vehicle) induced by the imiquimod 5% cream. As seen from FIG. 13, when treatment was performed with Compound 8 of the present invention dissolved in ethanol and the cream containing 0.5% Compound 8 of the present invention for 6 days, erythema increased by imiquimod was significantly reduced. Particularly, as seen from FIG. 14, when comparing erythema on day 14 after treatment with Compound 8, the reduction level was very remarkable, and as seen from FIG. 15, as a result of comparing change of the tissues observed with H&E staining, the thickness of stratum corneum of the experimental group on which Compound and the cream containing Compound 8 were applied was significantly reduced. In addition, as seen from FIG. 16, when the weight change after treatment with Compound 8 of the present invention was observed, numerical values almost similar to those of the control group were shown.

Accordingly, it is recognized that Compound 8 of the present invention is very effective in psoriasis treatment, and thus, Compound 8 of the present invention may be used as an external preparation for treating psoriasis.

EXAMPLE 16

Effect of Treatment With Compound 8 of The Present Invention on Transepidermal Water Loss (Tewl)

It was confirmed that the TEWL value which was significantly increased by the treatment with 5% imiquimod was remarkably reduced when applying Compound 8 of the present invention dissolved in ethanol and the cream containing 0.5% Compound 8 of the present invention for 5 days, which is shown in FIG. 17. As seen from FIG. 17, it is recognized that Compound 8 of the present invention is effective in enhanced moisturization of skin with psoriasis.

EXAMPLE 17

Reduced Thickness of Ear By Compound 8 of The Present Invention

Difference in the thickness between the untreated left ear and the right ear treated with the imiquimod-free cream and ethanol was not observed in the untreated control. However, significant thickness reduction of the right ear on which Compound 8 of the present invention dissolved in ethanol and the cream containing 0.5% Compound 8 of the present invention were applied as compared with the left ear treated with 5% imiquimod and ethanol was confirmed, which is shown in FIG. 18. As seen from FIG. 18, it is recognized that Compound 8 of the present invention is effective in treatment of inflammatory skin diseases including psoriasis, as in the TEWL results.

The invention claimed is:

1. An autophagy activation-inducing compound represented by the following Chemical Formula 1:

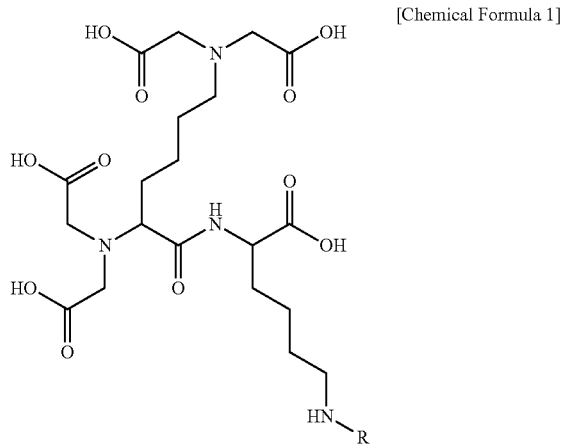

[Chemical Formula 1]

wherein
R is hydrogen or —X—$R^1$; X is a single bond or —CO—; and $R^1$ is C1-C20 substituted or unsubstituted alkyl,
or pharmaceutically acceptable salt thereof.

2. The autophagy activation-inducing compound or pharmaceutically acceptable salt thereof of claim 1, wherein it is an autophagy activation-inducing compound represented by the following Chemical Formula 2:

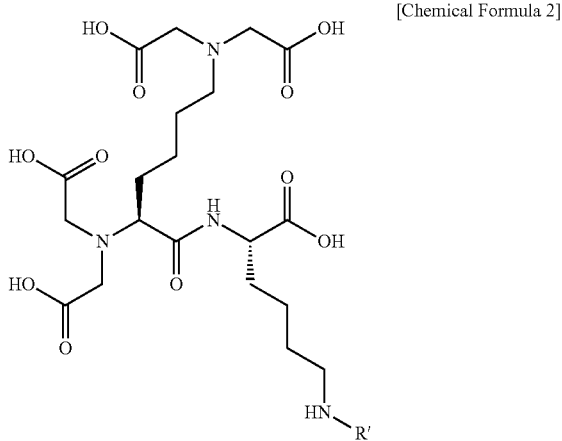

[Chemical Formula 2]

wherein
R' is hydrogen or —X—$R^2$; X is a single bond or —CO—; and $R^2$ is C1-C20 substituted or unsubstituted alkyl.

3. The autophagy activation-inducing compound or pharmaceutically acceptable salt thereof of claim 2, wherein X is —CO—, and $R^2$ is C1-C20 substituted or unsubstituted alkyl.

4. A medicinal composition for treatment and prevention of atopy or psoriasis skin diseases comprising the autophagy activation-inducing compound or pharmaceutically acceptable salt thereof of claim 1.

5. A medicinal composition for treatment and prevention of type II diabetes comprising the autophagy activation-inducing compound or pharmaceutically acceptable salt thereof of claim 1.

6. A medicinal composition for treatment and prevention of neurodegenerative diseases comprising the autophagy activation-inducing compound or pharmaceutically acceptable salt thereof of claim 1.

7. The medicinal composition of claim 6, wherein the neurodegenerative diseases are Alzheimer's disease, Huntington's disease, or Parkinson's disease.

8. The medicinal composition of claim 4, wherein the compound
or pharmaceutically acceptable salt thereof is comprised at 0.0001 to 10 wt. %.

9. The medicinal composition of claim 4, wherein it is used in a form of tablets, pills, capsules, granules, pulverized forms, powders, liquids, patches, coating agents or injections.

10. A cosmetic composition comprising the autophagy activation-inducing compound or pharmaceutically acceptable salt thereof of claim 1.

11. The cosmetic composition of claim 10, wherein the autophagy activation-inducing compound or pharmaceutically acceptable salt thereof is comprised at 0.0001 to 1 wt. %.

12. The cosmetic composition of claim 10, wherein the composition is at least one selected from the group consisting of a formulation of suspension, emulsion, paste, gel, cream, lotion, powder, soap, surfactant-containing cleansing, oil, powder foundation, emulsion foundation, wax foundation and spray.

13. A food composition comprising the autophagy activation-inducing compound or pharmaceutically acceptable salt thereof of claim 1.

14. A medicinal composition for treatment and prevention of atopy or psoriasis skin diseases comprising the autophagy activation-inducing compound or pharmaceutically acceptable salt thereof of claim 2.

15. A medicinal composition for treatment and prevention of atopy or psoriasis skin diseases comprising the autophagy activation-inducing compound or pharmaceutically acceptable salt thereof of claim 3.

16. A medicinal composition for treatment and prevention of type II diabetes comprising the autophagy activation-inducing compound or pharmaceutically acceptable salt thereof of claim 2.

17. A medicinal composition for treatment and prevention of type II diabetes comprising the autophagy activation-inducing compound or pharmaceutically acceptable salt thereof of claim 3.

18. A medicinal composition for treatment and prevention of neurodegenerative diseases comprising the autophagy activation-inducing compound or pharmaceutically acceptable salt thereof of claim 2.

19. A medicinal composition for treatment and prevention of neurodegenerative diseases comprising the autophagy activation-inducing compound or pharmaceutically acceptable salt thereof of claim 3.

20. A cosmetic composition comprising the autophagy activation-inducing compound or pharmaceutically acceptable salt thereof of claim 2.

21. A cosmetic composition comprising the autophagy activation-inducing compound or pharmaceutically acceptable salt thereof of claim 3.

22. A food composition comprising the autophagy activation-inducing compound or pharmaceutically acceptable salt thereof of claim 2.

23. A food composition comprising the autophagy activation-inducing compound or pharmaceutically acceptable salt thereof of claim 3.

* * * * *